(12) United States Patent
Hirsch et al.

(10) Patent No.: US 12,201,697 B2
(45) Date of Patent: *Jan. 21, 2025

(54) AAV-IDUA VECTOR FOR TREATMENT OF MPS I-ASSOCIATED BLINDNESS

(71) Applicant: The University of North Carolina at Chapel Hill, Chapel Hill, NC (US)

(72) Inventors: Matthew Louis Hirsch, Chapel Hill, NC (US); Richard Jude Samulski, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 262 days.

This patent is subject to a terminal disclaimer.

(21) Appl. No.: 17/407,718

(22) Filed: Aug. 20, 2021

(65) Prior Publication Data
US 2022/0047721 A1 Feb. 17, 2022

Related U.S. Application Data

(62) Division of application No. 16/076,654, filed as application No. PCT/US2017/018829 on Feb. 22, 2017, now Pat. No. 11,116,850.

(60) Provisional application No. 62/298,126, filed on Feb. 22, 2016.

(51) Int. Cl.
| | |
|---|---|
| *A61K 48/00* | (2006.01) |
| *A61K 9/00* | (2006.01) |
| *A61K 35/76* | (2015.01) |
| *A61P 27/00* | (2006.01) |
| *C07K 14/00* | (2006.01) |
| *C12N 9/24* | (2006.01) |
| *C12N 9/26* | (2006.01) |
| *C12N 15/86* | (2006.01) |

(52) U.S. Cl.
CPC ............ *A61K 48/00* (2013.01); *A61K 9/0019* (2013.01); *A61K 9/0048* (2013.01); *A61K 35/76* (2013.01); *A61P 27/00* (2018.01); *C07K 14/00* (2013.01); *C12N 9/2402* (2013.01); *C12N 9/2411* (2013.01); *C12N 15/86* (2013.01); *C12Y 302/01076* (2013.01); *C12N 2710/10044* (2013.01); *C12N 2750/14141* (2013.01); *C12N 2750/14143* (2013.01); *C12N 2800/22* (2013.01)

(58) Field of Classification Search
None
See application file for complete search history.

(56) References Cited

U.S. PATENT DOCUMENTS

| | | |
|---|---|---|
| 2012/0288489 A1 | 11/2012 | Wolf et al. |
| 2013/0158103 A1 | 6/2013 | Mohan |
| 2017/0130245 A1 | 5/2017 | Kotin et al. |

FOREIGN PATENT DOCUMENTS

| | | |
|---|---|---|
| CN | 105026554 A | 11/2015 |
| EP | 1325138 A2 | 7/2003 |
| RU | 2013115853 A | 11/2014 |
| WO | 0168888 A2 | 9/2001 |
| WO | 2001068888 | 9/2001 |
| WO | 2014151341 A1 | 9/2014 |
| WO | 2015191508 A1 | 12/2015 |
| WO | 2016005514 A1 | 1/2016 |

OTHER PUBLICATIONS

Vance et al. Blood (Dec. 2015) 126(23):2041 (Year: 2015).*
"Examination Report corresponding to European Application No. 17757103.1 dated Sep. 11, 2020".
"Extended European Search Report corresponding to European Application No. 17757103.1 dated Jul. 5, 2019".
"International Preliminary Report on Patentability corresponding to International Application No. PCT/US2017/018829 mailed Sep. 7, 2018".
"Notification of Transmittal of the International Search Report and the Written Opinion of the International Searching Authority, or the Declaration corresponding to International Application No. PCT/US2017/018829 mailed Jun. 8, 2017".
"Office Action corresponding to Israeli Application No. 260,643 issued Jul. 20, 2021".
"Office Action corresponding to Japanese Application No. 2018-563395 issued Feb. 17, 2021".
"Office Action corresponding to Russian Application No. 2018132517 issued Jun. 10, 2020".
Acosta, et al., ""RTB Lectin: a novel receptor-independent delivery system for lysosomal enzyme replacement therapies",", Scientific Reports 5(14144):1-11 (2015).
Beck , "Mucopolysaccharidosis I", Orphanet Encyclopedia http://www.orpha.net/data/patho/GB/us-MPSI (2003) 3 pages.
Hinderer , et al., ""Intrathecal Gene Therapy Corrects CNS Pathology in a Feline Model of Mucopolysaccharidosis I",", Molecular Therapy 22(12):2018-2027 (2014).
Hinderer, Christian , et al., "Liver-directed gene therapy corrects cardiovascular lesions in feline mucopolysaccharidosis in Type 1", PNAS 111(41):14894-14899 (2014).
Janson , et al., ""Comparison of Endovascular and Intraventricular Gene Therapy With Adeno-Associated Virus-alpha-L-Iduronidase for Hurler Disease",", Neurosurgery 74(1):99-111 (2014).
Naso, Michael F, et al., "Adeno-Associated Virus (AAV) as a Vector for Gene Therapy", BioDrugs 31:317-334 (2017).
Scott, H.S. , et al., "Human alpha-L-iduronidase: cDNA isolation and expression", Proc. Natl. Acad. Sci. USA 88:9695-9699 (Nov. 1991).
Vance, Melissa A, et al., "AAV gene therapy for MPS1 corneal clouding and joint stiffness", Blood 126(23):2041 (Dec. 3, 2015).
Wolf , et al., ""Direct Gene Transfer to the CNS Prevents Emergence of Neurologic Disease in a Murine Model of Mucopolysaccharidosis Type I",", Neurobiol Dis. 43(1):123-133 (2011).

(Continued)

*Primary Examiner* — Marcia S Noble
(74) *Attorney, Agent, or Firm* — Myers Bigel, P.A.

(57) ABSTRACT

This invention relates to viral vectors for delivery of alpha-L-iduronidase to the cornea of a subject and methods of using the same for treatment and prevention of corneal clouding and blindness in a subject due to mucopolysaccharidosis I.

17 Claims, 10 Drawing Sheets

Specification includes a Sequence Listing.

(56) References Cited

OTHER PUBLICATIONS

"Office Action corresponding to Canadian Application No. 3,011,943 dated Feb. 17, 2023".
"Office Action corresponding to Chinese Application No. 201780012623.2 issued Feb. 22, 2022".
Hirsch, Matthew, et al., "AAV Gene Therapy for MPS1 Corneal Clouding", Investigative Ophthalmology & Visual Science 56(7):260 (Jun. 2015).
"Office Action corresponding to Chinese Application No. 201780012623.2 issued Sep. 23, 2021".
"Office Action corresponding to Australian Application No. 2017223465 dated Apr. 5, 2023".
"Office Action corresponding to Mexican Application No. MX/a/2018/009426 issued Apr. 5, 2023".
"Office Action corresponding to Russian Application No. 2018132517 issued Dec. 16, 2021".
Fenzl, Carlton R, et al., "Ocular manifestations and management recommendations of lysosomal storage disorders I : mucopolysaccharidoses", Clinical Ophthalmology 9:1633-1644 (Sep. 7, 2015).
Gain, Philippe, et al., "Global Survey of Corneal Transplantation and Eye Banking", JAMA Ophthalmology 134(2):167-173 (Feb. 2016).
Scalabrino, Miranda L, et al., "Intravitreal delivery of a novel AAV vector targets ON bipolar cells and restores visual function in a mouse model of complete congenital stationary night blindness", Human Molecular Genetics 24(21):6229-6239 (Aug. 26, 2015).
Watson, G, et al., "Intrathecal administration of AAV vectors for the treatment of lysosomal storage in the brains of MPS I mice", Gene Therapy 13:917-925 (Feb. 16, 2006).
"Office Action corresponding to Japanese Application No. 2018-563395 mailed Nov. 19, 2021".
"Office Action corresponding to Russian Application No. 2018132517 issued Mar. 10, 2023".
Miyadera, Keiko, et al., "Intrastromal Gene Therapy Prevents and Reverses Advanced Corneal Clouding in a Canine Model of Mucopolysaccharidosis I", Molecular Therapy 28(6):1455-1463 (Jun. 2020).
Yuan, Ching, et al., "A novel explanation of corneal clouding in a bone marrow transplant-treated patient with Hurler syndrome", Experimental Eye Research 148:83-89 (May 26, 2016).
"Office Action corresponding to Brazilian Application No. 112018017125-5 issued Aug. 26, 2022".
"Office Action corresponding to Japanese Application No. 2018-563395 issued Aug. 8, 2022".
"Office Action corresponding to Japanese Application No. 2022-177564 mailed Sep. 14, 2023".
"Office Action corresponding to Mexican Application No. MX/a/2018/009426 issued Nov. 15, 2023".
Beck, Michael, et al., "The natural history of MPS I: global perspectives from the MPS I Registry", Genet. Med. 16(10):759-765 (Oct. 2014).
"Office Action corresponding to Canadian Application No. 3,011,943 dated Jun. 6, 2024".
"Office Action corresponding to Korean Application No. 10-2018-7023851 issued Oct. 16, 2024",.

* cited by examiner

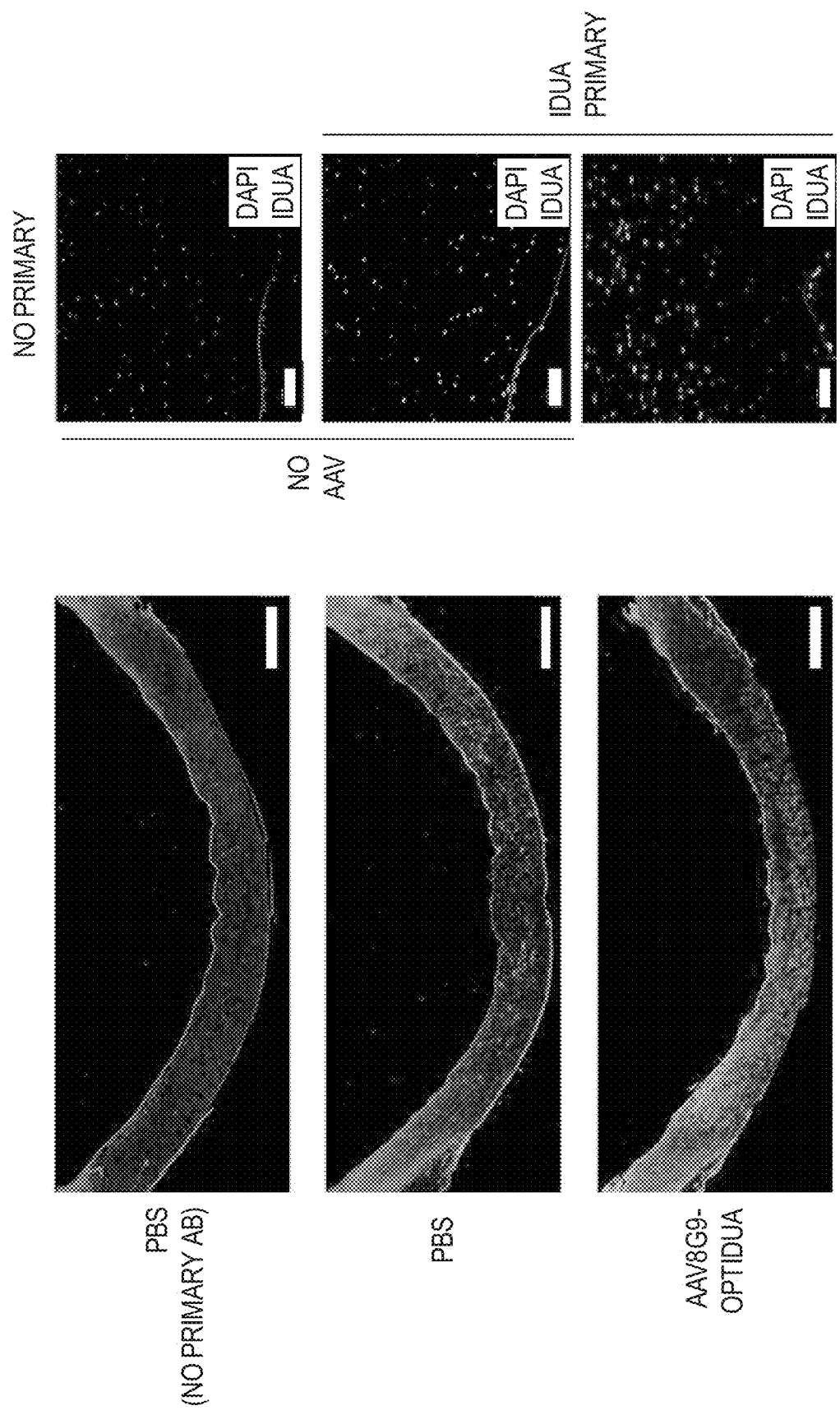

FIG. 8A    FIG. 8B
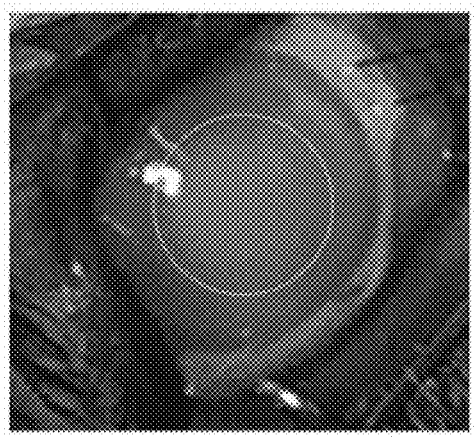
FIG. 8C    FIG. 8D
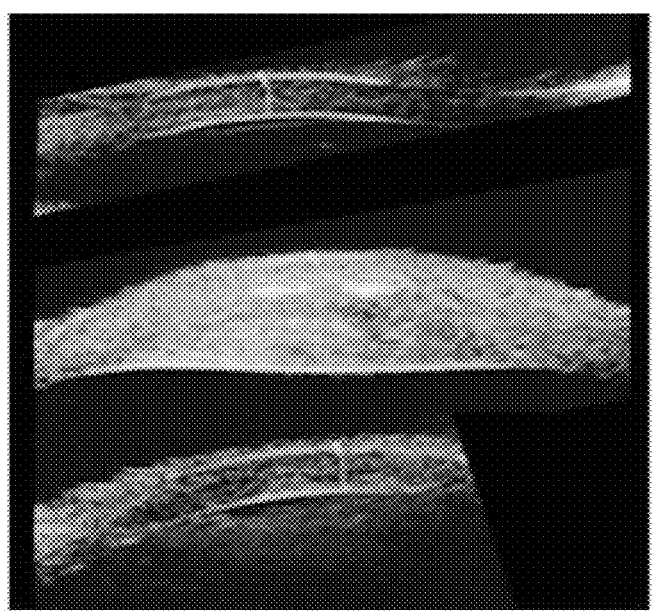
CENTRAL CORNEA THICKNESS
0.79 mm
2.19 mm
0.86 mm
FIG. 8E

AAV-IDUA VECTOR FOR TREATMENT OF MPS I-ASSOCIATED BLINDNESS

STATEMENT OF PRIORITY

This application is a divisional of and claims priority to U.S. patent application Ser. No. 16/076,654 filed Aug. 8, 2018, which is a 35 U.S.C. § 371 national phase application of PCT Application PCT/US2017/018829 filed Feb. 22, 2017, which claims the benefit of U.S. Provisional Application Ser. No. 62/298,126, filed Feb. 22, 2016, the entire contents of each of which are incorporated by reference herein in its entirety.

GOVERNMENT INTEREST

This invention was made with government support under Grant Number AI072176, AR064369 awarded by the National Institutes of Health. The government has certain rights in the invention.

STATEMENT REGARDING ELECTRONIC FILING OF A SEQUENCE LISTING

A Sequence Listing in ASCII text format, submitted under 37 C.F.R. § 1.821, entitled 5470.772DV_ST25.txt, 3,502 bytes in size, generated on Aug. 20, 2021 and filed via EFS-Web, is provided in lieu of a paper copy. This Sequence Listing is hereby incorporated by reference into the specification for its disclosures.

FIELD OF THE INVENTION

This invention relates to viral vectors for delivery of alpha-L-iduronidase to the cornea of a subject and methods of using the same for treatment and prevention of corneal clouding and blindness in a subject due to mucopolysaccharidosis I.

BACKGROUND OF THE INVENTION

Mucopolysaccharidosis I (MPS I) is an autosomal recessive lysosomal storage disorder caused by null or nonsense mutations in the gene encoding alpha-L-iduronidase (IDUA), a ubiquitous intracellular and secreted enzyme that breaks down glycosaminoglycans (GAGs). In the absence of functional IDUA, GAGs accumulate in lysosomes and disrupt the normal intracellular trafficking of lipids, sugars, and proteins causing multisystem end organ damage. The incidence of MPS I is approximately 1 in 100,000 and the disease is characterized by hepatosplenomegaly, cardiac insufficiency, bone and joint deformities, dwarfism, mental retardation and serious nervous system problems, which commonly result in death by 10 years of age. Additional symptoms include hearing loss, joint stiffness, and clouding of the cornea which results in loss of vision (Aldenhoven et al., *Blood* 125(13):2164 (2015)).

Current MPS I treatments include IDUA enzyme replacement therapy (ERT) (ALDURAZYME®) via intravenous injections, which has proven useful in reducing hepatosplenomegaly, and in improving myocardiac function, pulmonary symptoms and motility in MPS I patients with mild disease. A more promising treatment relies on allogeneic hematopoietic stem cell transplantation (HSCT) which has been used for the past 2-3 decades in MPS I patients. HSCT has proven successful at improving cognitive function, reducing hepatosplenomegaly, preventing ischemic cardiac disease and prolonging the patient's lifespan, in some cases by decades. Clinical outcomes are best when myeloablative chemotherapy and cord blood donors are utilized and also correlates with the extent of sustained donor chimerism. A third MPS I treatment approach that is still under preclinical evaluation relies on an adeno-associated virus (AAV) IDUA gene addition strategy. Central nervous system targeted AAV-IDUA gene therapy has been explored in murine, feline, and canine MPS I models following administration via several routes including the carotid artery, intraparenchymal, intraventricular and intrathecal (Janson et al., *Neurosurgery* 74(1):99 (2014); Wolf et al., *Neurobiol. Dis.* 43(1):123 (2011); Hinderer et al., *Mol. Ther.* 22(12):2018 (2014)). These gene therapy studies independently report histological, biochemical, and in particular cognitive improvements while IDUA-related toxicity was not observed. However, ERT, HSCT and AAV CNS-targeted or systemic gene therapy exhibit a common deficiency; which is the inability to correct MPS I-associated maladies in privileged compartments including the joint and eye.

Regarding the ocular abnormalities, approximately 90% of MPS I children lose vision due to corneal clouding, which has been attributed to the abnormal presence of vacuolated stroma cells (Huang et al., *Exp. Eye Res.* 62(4):377 (1996)). Detailed analyses of MPS I human corneas demonstrated an accumulation of chondroitin and dermatan sulphate GAGs, which alter the uniform distribution, organization, and size of collagen fibrils (Alroy et al., *Exp. Eye Res.* 68(5):523 (1999); Fahnehjelm et al., *Acta Ophthalmol. Scand.* 84(6): 781 (2006)). Cornea transplantation in MPS I children has been used to address the corneal blindness, however the high rejection rate has, in recent years, discouraged this treatment as standard practice. On the contrary, isolated reports using HSCT have demonstrated the capacity to stabilize, improve, and in some cases restore corneal clarity (Fahnehjelm et al., *Acta Ophthalmol. Scand.* 84(6):781 (2006); Hobbs, *Lancet* 2(8249):735 (1981); Hoogerbrugge et al., *Lancet,* 345 (8962):1398 (1995); Vellodi et al., *Arch. Dis. Child.* 76(2): 92 (1997); Gullingsrud et al., *Ophthalmology,* 105(6):1099 (1998); Souillet et al., *Bone Marrow Transplant* 31(12):1105 (2003)).

The present invention provides viral vectors for expression of IDUA in the cornea and methods for treating or preventing MPS I-associated corneal clouding and blindness.

SUMMARY OF THE INVENTION

This invention is based on the finding that the use of AAV vectors for delivery of IDUA to the cornea of a subject with MPS I is effective to express IDUA throughout the cornea. Thus, one aspect of the invention relates to a recombinant nucleic acid comprising a nucleotide sequence encoding human alpha-L-iduronidase (IDUA), wherein the nucleotide sequence has been codon-optimized for expression in human cells.

Another aspect of the invention relates to an AAV vector genome comprising the nucleic acid of the invention, an AAV particle comprising the AAV vector genome, and a pharmaceutical composition comprising the AAV particle.

A further aspect of the invention relates to a method of producing a recombinant AAV particle comprising an AAV capsid, the method comprising: providing a cell in vitro with an AAV Cap and AAV Rep coding sequences, the AAV vector genome of the invention, and helper functions for generating a productive AAV infection; and allowing assembly of the recombinant AAV particle comprising the AAV capsid and encapsidating the AAV vector genome.

An additional aspect of the invention relates to a method of delivering IDUA to the cornea of a subject, comprising administering to the cornea of the subject an effective amount of an AAV particle that expresses IDUA, thereby delivering IDUA to the cornea of the subject.

Another aspect of the invention relates to a method of treating or delaying the onset of MPS I-associated corneal clouding in a subject in need thereof, comprising administering to the cornea of the subject a therapeutically effective amount of an AAV particle that expresses IDUA, thereby treating or delaying the onset of MPS I-associated corneal clouding in the subject.

These and other aspects of the invention are set forth in more detail in the description of the invention below.

BRIEF DESCRIPTION OF THE DRAWINGS

FIGS. 6A-6B show distribution of IDUA protein following AAV-8G9-opt-IDUA transduction. (A) Immunofluorescence image showing the distribution of IDUA protein across a human cornea section seven days post-injection of AAV8G9-opt-IDUA or PBS (vehicle). The images were obtained with 10× objective and assembled by stitch processing. The scale bar is equal to 2000 μm. DAPI was used for nuclei counterstain. (B) Cross section of the same stained human corneas but taken with a 20× objective. The top figure corresponds to the negative control of staining, which was performed exactly in the same as the other samples but without the primary antibody. DAPI was used for nuclei counterstain. The scale bar is equal to 100 μm.

FIGS. 8A-8E show intrastromal injection of AAV8G9-optIDUA in MPS1 canines. The left eye of dog 1-712 was injected with the AAV8G9-CMV-optIDUA (1e9 vg/μl) solution. The needle tip of an insulin syringe was inserted into the corneal stroma (A) and the solution was injected gradually (B) until the full volume (65 μl) was administered (C). Immediately following the injection, an area of fluid retention was visible as clouding or edema of the axial cornea, covering 30% of the corneal surface (D). (E) Ophthalmic ultrasound biomicroscopy allowed determination of central cornea thickness at the indicated timepoints.

DETAILED DESCRIPTION OF THE INVENTION

Figure 1A:
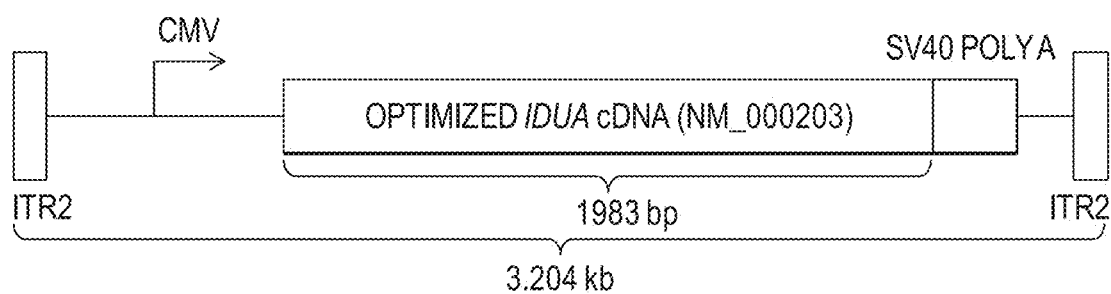
FIGS. 1A-1D show restoration of IDUA activity in MPS I patient fibroblasts by AAV gene therapy. (A) Schematic diagram of the AAV-IDUA optimized vector construct. (B) Cell lysates (Left panel) and supernatants (Right panel) from AAV2 infected and non-infected fibroblasts, normal human fibroblasts (NHF) or MPS I fibroblasts, were analyzed for IDUA protein expression. Detection of β-actin was performed as a loading control of total protein in cell lysates. (C,D) Functional activity of IDUA protein was obtained for cell lysis (C) and supernatants (D) from AAV2 infected and not-infected fibroblasts, NHF or MPS I fibroblasts. For cell lysis, the nmoles of 4-MU were normalized to one hour reaction and mg total protein. For cell supernatants, the nmoles of 5-MU were normalized to 10 μl of the sample. 4-MU, 4-methylumbelliferone; CMV, cytomegalovirus promoter; ITR, internal terminal repeats; GFP, Green fluorescence protein.

The present invention will now be described with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. All publications, patent applications, patents, and other references mentioned herein are incorporated by reference in their entirety.

Nucleotide sequences are presented herein by single strand only, in the 5' to 3' direction, from left to right, unless specifically indicated otherwise. Nucleotides and amino acids are represented herein in the manner recommended by the IUPAC-IUB Biochemical Nomenclature Commission, or (for amino acids) by either the one-letter code, or the three letter code, both in accordance with 37 CFR § 1.822 and established usage. See, e.g., *Patent In User Manual,* 99-102 (November 1990) (U.S. Patent and Trademark Office).

Except as otherwise indicated, standard methods known to those skilled in the art may be used for the construction of recombinant parvovirus and AAV (rAAV) constructs, packaging vectors expressing the parvovirus Rep and/or Cap sequences, and transiently and stably transfected packaging cells. Such techniques are known to those skilled in the art. See, e.g., SAMBROOK et al., MOLECULAR CLONING: A LABORATORY MANUAL 2nd Ed. (Cold Spring Harbor, N.Y., 1989); AUSUBEL et al., CURRENT PROTOCOLS IN MOLECULAR BIOLOGY (Green Publishing Associates, Inc. and John Wiley & Sons, Inc., New York).

Moreover, the present invention also contemplates that in some embodiments of the invention, any feature or combination of features set forth herein can be excluded or omitted.

To illustrate further, if, for example, the specification indicates that a particular amino acid can be selected from A, G, I, L and/or V, this language also indicates that the amino acid can be selected from any subset of these amino acid(s) for example A, G, I or L; A, G, I or V; A or G; only L; etc. as if each such subcombination is expressly set forth herein. Moreover, such language also indicates that one or more of the specified amino acids can be disclaimed. For example, in particular embodiments the amino acid is not A, G or I; is not A; is not G or V; etc. as if each such possible disclaimer is expressly set forth herein.

Definitions

The following terms are used in the description herein and the appended claims.

The singular forms "a" and "an" are intended to include the plural forms as well, unless the context clearly indicates otherwise.

Furthermore, the term "about," as used herein when referring to a measurable value such as an amount of the length of a polynucleotide or polypeptide sequence, dose, time, temperature, and the like, is meant to encompass variations of 20%, 10%, 5%, 1%, 0.5%, or even 0.1% of the specified amount.

Also as used herein, "and/or" refers to and encompasses any and all possible combinations of one or more of the associated listed items, as well as the lack of combinations when interpreted in the alternative ("or").

As used herein, the transitional phrase "consisting essentially of" is to be interpreted as encompassing the recited materials or steps "and those that do not materially affect the basic and novel characteristic(s)" of the claimed invention (e.g., rAAV replication). Thus, the term "consisting essentially of" as used herein should not be interpreted as equivalent to "comprising."

The term "consists essentially of" (and grammatical variants), as applied to a polynucleotide or polypeptide sequence of this invention, means a polynucleotide or polypeptide that consists of both the recited sequence (e.g., SEQ ID NO) and a total of ten or less (e.g., 1, 2, 3, 4, 5, 6, 7, 8, 9, or 10) additional nucleotides or amino acids on the 5' and/or 3' or N-terminal and/or C-terminal ends of the recited sequence such that the function of the polynucleotide or polypeptide is not materially altered. The total of ten or less additional nucleotides or amino acids includes the total number of additional nucleotides or amino acids on both ends added together. The term "materially altered," as applied to polynucleotides of the invention, refers to an increase or decrease in ability to express the encoded polypeptide of at least about 50% or more as compared to the expression level of a polynucleotide consisting of the recited sequence. The term "materially altered," as applied to polypeptides of the invention, refers to an increase or decrease in enzymatic activity of at least about 50% or more as compared to the activity of a polypeptide consisting of the recited sequence.

The term "parvovirus" as used herein encompasses the family Parvoviridae, including autonomously-replicating parvoviruses and dependoviruses. The autonomous parvoviruses include members of the genera Parvovirus, Erythrovirus, Densovirus, Iteravirus, and Contravirus. Exemplary autonomous parvoviruses include, but are not limited to, minute virus of mouse, bovine parvovirus, canine parvovirus, chicken parvovirus, feline panleukopenia virus, feline parvovirus, goose parvovirus, H1 parvovirus, muscovy duck parvovirus, snake parvovirus, and B19 virus. Other autonomous parvoviruses are known to those skilled in the art. See, e.g., FIELDS et al., VIROLOGY, volume 2, chapter 69 (4th ed., Lippincott-Raven Publishers).

The genus *Dependovirus* contains the adeno-associated viruses (AAV), including but not limited to, AAV type 1, AAV type 2, AAV type 3 (including types 3A and 3B), AAV type 4, AAV type 5, AAV type 6, AAV type 7, AAV type 8, AAV type 9, AAV type 10, AAV type 11, AAV type 12, AAV type 13, avian AAV, bovine AAV, canine AAV, goat AAV, snake AAV, equine AAV, and ovine AAV. See, e.g., FIELDS et al., VIROLOGY, volume 2, chapter 69 (4th ed., Lippincott-Raven Publishers); and Table 1.

As used herein, the term "adeno-associated virus" (AAV), includes but is not limited to, AAV type 1, AAV type 2, AAV type 3 (including types 3A and 3B), AAV type 4, AAV type 5, AAV type 6, AAV type 7, AAV type 8, AAV type 9, AAV type 10, AAV type 11, AAV type 12, AAV type 13, snake AAV, avian AAV, bovine AAV, canine AAV, equine AAV, ovine AAV, goat AAV, shrimp AAV, and any other AAV now known or later discovered. See, e.g., FIELDS et al., VIROLOGY, volume 2, chapter 69 (4th ed., Lippincott-Raven Publishers). A number of relatively new AAV serotypes and clades have been identified (See, e.g., Gao et al., (2004) *J. Virol.* 78:6381; Moris et al., (2004) *Virol.* 33-:375; and Table 1).

The parvovirus vectors, particles, and genomes of the present invention can be from, but are not limited to, AAV. The genomic sequences of various serotypes of AAV and the autonomous parvoviruses, as well as the sequences of the native ITRs, Rep proteins, and capsid subunits are known in the art. Such sequences may be found in the literature or in public databases such as GenBank. See, e.g., GenBank Accession Numbers NC_002077, NC_001401, NC_001729, NC_001863, NC_001829, NC_001862, NC_000883, NC_001701, NC_001510, NC_006152, NC_006261, AF063497, U89790, AF043303, AF028705, AF028704, J02275, J01901, J02275, X01457, AF288061, AH009962, AY028226, AY028223, AY631966, AX753250, EU285562, NC_001358, NC_001540, AF513851, AF513852 and AY530579; the disclosures of which are incorporated by reference herein for teaching parvovirus and AAV nucleic acid and amino acid sequences. See also, e.g., Bantel-Schaal et al., (1999) *J Virol*. 73: 939; Chiorini et al., (1997) *J. Virol*. 71:6823; Chiorini et al., (1999) *J. Virol*. 73:1309; Gao et al., (2002) *Proc. Nat. Acad. Sci. USA* 99:11854; Moris et al., (2004) *Virol*. 33-:375-383; Mori et al., (2004) *Virol*. 330: 375; Muramatsu et al., (1996) *Virol*. 221:208; Ruffing et al., (1994) *J. Gen. Virol*. 75:3385; Rutledge et al., (1998) *J. Virol*. 72:309; Schmidt et al., (2008) *J. Virol*. 82:8911; Shade et al., (1986) *J. Virol*. 58:921; Srivastava et al., (1983) *J. Virol*. 45:555; Xiao et al., (1999) *J. Virol*. 73:3994; international patent publications WO 00/28061, WO 99/61601, WO 98/11244; and U.S. Pat. No. 6,156,303; the disclosures of which are incorporated by reference herein for teaching parvovirus and AAV nucleic acid and amino acid sequences. See also Table 1. An early description of the AAV1, AAV2 and AAV3 ITR sequences is provided by Xiao, X., (1996), "Characterization of Adeno-associated virus (AAV) DNA replication and integration," Ph.D. Dissertation, University of Pittsburgh, Pittsburgh, Pa. (incorporated herein in its entirety).

The term "tropism" as used herein refers to entry of the virus into the cell, optionally and preferably followed by expression (e.g., transcription and, optionally, translation) of sequences carried by the viral genome in the cell, e.g., for a recombinant virus, expression of the heterologous nucleotide sequences(s). Those skilled in the art will appreciate that transcription of a heterologous nucleic acid sequence from the viral genome may not be initiated in the absence of trans-acting factors, e.g., for an inducible promoter or otherwise regulated nucleic acid sequence. In the case of AAV, gene expression from the viral genome may be from a stably integrated provirus, from a non-integrated episome, as well as any other form in which the virus may take within the cell.

As used herein, "transduction" of a cell by parvovirus or AAV refers to parvovirus/AAV-mediated transfer of genetic material into the cell. See, e.g., FIELDS et al., *VIROLOGY*, volume 2, chapter 69 (3d ed., Lippincott-Raven Publishers).

The terms "5' portion" and "3' portion" are relative terms to define a spatial relationship between two or more elements. Thus, for example, a "3' portion" of a polynucleotide indicates a segment of the polynucleotide that is downstream of another segment. The term "3' portion" is not intended to indicate that the segment is necessarily at the 3' end of the polynucleotide, or even that it is necessarily in the 3' half of the polynucleotide, although it may be. Likewise, a "5' portion" of a polynucleotide indicates a segment of the polynucleotide that is upstream of another segment. The term "5' portion" is not intended to indicate that the segment is necessarily at the 5' end of the polynucleotide, or even that it is necessarily in the 5' half of the polynucleotide, although it may be.

As used herein, the term "polypeptide" encompasses both peptides and proteins, unless indicated otherwise.

A "polynucleotide" is a sequence of nucleotide bases, and may be RNA, DNA or DNA-RNA hybrid sequences (including both naturally occurring and non-naturally occurring nucleotides), and can be either single or double stranded DNA sequences.

The term "sequence identity," as used herein, has the standard meaning in the art. As is known in the art, a number of different programs can be used to identify whether a polynucleotide or polypeptide has sequence identity or similarity to a known sequence. Sequence identity or similarity may be determined using standard techniques known in the art, including, but not limited to, the local sequence identity algorithm of Smith & Waterman, *Adv. Appl. Math.* 2:482 (1981), by the sequence identity alignment algorithm of Needleman & Wunsch, *J. Mol. Biol.* 48:443 (1970), by the search for similarity method of Pearson & Lipman, *Proc. Natl. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., *Nucl. Acid Res.* 12:387 (1984), preferably using the default settings, or by inspection.

TABLE 1

| Complete Genomes | GenBank Accession Number |
| --- | --- |
| Adeno-associated virus 1 | NC_002077, AF063497 |
| Adeno-associated virus 2 | NC_001401 |
| Adeno-associated virus 3 | NC_001729 |
| Adeno-associated virus 3B | NC_001863 |
| Adeno-associated virus 4 | NC_001829 |
| Adeno-associated virus 5 | Y18065, AF085716 |
| Adeno-associated virus 6 | NC_001862 |
| Avian AAV ATCC VR-865 | AY186198, AY629583, NC_004828 |
| Avian AAV strain DA-1 | NC_006263, AY629583 |
| Bovine AAV | NC_005889, AY388617 |
| Clade A | |
| AAV1 | NC_002077, AF063497 |
| AAV6 | NC_001862 |
| Hu.48 | AY530611 |
| Hu43 | AY530606 |
| Hu44 | AY530607 |
| Hu46 | AY530609 |
| Clade B | |
| Hu.19 | AY530584 |
| Hu.20 | AY530586 |
| Hu23 | AY530589 |
| Hu22 | AY530588 |
| Hu24 | AY530590 |
| Hu21 | AY530587 |
| Hu27 | AY530592 |
| Hu28 | AY530593 |
| Hu29 | AY530594 |
| Hu63 | AY530624 |
| Hu64 | AY530625 |
| Hu13 | AY530578 |
| Hu56 | AY530618 |
| Hu57 | AY530619 |
| Hu49 | AY530612 |
| Hu58 | AY530620 |
| Hu34 | AY530598 |
| Hu35 | AY530599 |
| AAV2 | NC_001401 |
| Hu45 | AY530608 |
| Hu47 | AY530610 |
| Hu51 | AY530613 |
| Hu52 | AY530614 |
| HuT41 | AY695378 |
| HuS17 | AY695376 |
| HuT88 | AY695375 |
| HuT71 | AY695374 |
| HuT70 | AY695373 |

TABLE 1-continued

| Complete Genomes | GenBank Accession Number |
|---|---|
| HuT40 | AY695372 |
| HuT32 | AY695371 |
| HuT17 | AY695370 |
| HuLG15 | AY695377 |
| Clade C | |
| Hu9 | AY530629 |
| Hu10 | AY530576 |
| Hu11 | AY530577 |
| Hu53 | AY530615 |
| Hu55 | AY530617 |
| Hu54 | AY530616 |
| Hu7 | AY530628 |
| Hu18 | AY530583 |
| Hu15 | AY530580 |
| Hu16 | AY530581 |
| Hu25 | AY530591 |
| Hu60 | AY530622 |
| Ch5 | AY243021 |
| Hu3 | AY530595 |
| Hu1 | AY530575 |
| Hu4 | AY530602 |
| Hu2 | AY530585 |
| Hu61 | AY530623 |
| Clade D | |
| Rh62 | AY530573 |
| Rh48 | AY530561 |
| Rh54 | AY530567 |
| Rh55 | AY530568 |
| Cy2 | AY243020 |
| AAV7 | AF513851 |
| Rh35 | AY243000 |
| Rh37 | AY242998 |
| Rh36 | AY242999 |
| Cy6 | AY243016 |
| Cy4 | AY243018 |
| Cy3 | AY243019 |
| Cy5 | AY243017 |
| Rh13 | AY243013 |
| Clade E | |
| Rh38 | AY530558 |
| Hu66 | AY530626 |
| Hu42 | AY530605 |
| Hu67 | AY530627 |
| Hu40 | AY530603 |
| Hu41 | AY530604 |
| Hu37 | AY530600 |
| Rh40 | AY530559 |
| Rh2 | AY243007 |
| Bb1 | AY243023 |
| Bb2 | AY243022 |
| Rh10 | AY243015 |
| Hu17 | AY530582 |
| Hu6 | AY530621 |
| Rh25 | AY530557 |
| Pi2 | AY530554 |
| Pi1 | AY530553 |
| Pi3 | AY530555 |
| Rh57 | AY530569 |
| Rh50 | AY530563 |
| Rh49 | AY530562 |
| Hu39 | AY530601 |
| Rh58 | AY530570 |
| Rh61 | AY530572 |
| Rh52 | AY530565 |
| Rh53 | AY530566 |
| Rh51 | AY530564 |
| Rh64 | AY530574 |
| Rh43 | AY530560 |
| AAV8 | AF513852 |
| Rh8 | AY242997 |
| Rh1 | AY530556 |

TABLE 1-continued

| Complete Genomes | GenBank Accession Number |
|---|---|
| Clade F | |
| Hu14 (AAV9) | AY530579 |
| Hu31 | AY530596 |
| Hu32 | AY530597 |
| Clonal Isolate | |
| AAV5 | Y18065, AF085716 |
| AAV3 | NC_001729 |
| AAV3B | NC_001863 |
| AAV4 | NC_001829 |
| Rh34 | AY243001 |
| Rh33 | AY243002 |
| Rh32 | AY243003 |

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, *J. Mol. Evol.* 35:351 (1987); the method is similar to that described by Higgins & Sharp, *CABIOS* 5:151 (1989).

Another example of a useful algorithm is the BLAST algorithm, described in Altschul et al., *J. Mol. Biol.* 215:403 (1990) and Karlin et al., *Proc. Natl. Acad. Sci. USA* 90:5873 (1993). A particularly useful BLAST program is the WU-BLAST-2 program which was obtained from Altschul et al., *Meth. Enzymol.*, 266:460 (1996); blast.wustl/edu/blast/README.html. WU-BLAST-2 uses several search parameters, which are preferably set to the default values. The parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al., *Nucleic Acids Res.* 25:3389 (1997).

A percentage amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

In a similar manner, percent nucleic acid sequence identity is defined as the percentage of nucleotide residues in the candidate sequence that are identical with the nucleotides in the polynucleotide specifically disclosed herein.

The alignment may include the introduction of gaps in the sequences to be aligned. In addition, for sequences which contain either more or fewer nucleotides than the polynucleotides specifically disclosed herein, it is understood that in one embodiment, the percentage of sequence identity will be determined based on the number of identical nucleotides in relation to the total number of nucleotides. Thus, for example, sequence identity of sequences shorter than a sequence specifically disclosed herein, will be determined using the number of nucleotides in the shorter sequence, in one embodiment. In percent identity calculations relative weight is not assigned to various manifestations of sequence variation, such as insertions, deletions, substitutions, etc.

In one embodiment, only identities are scored positively (+1) and all forms of sequence variation including gaps are assigned a value of "0," which obviates the need for a weighted scale or parameters as described below for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

As used herein, an "isolated" polynucleotide (e.g., an "isolated DNA" or an "isolated RNA") means a polynucleotide separated or substantially free from at least some of the other components of the naturally occurring organism or virus, for example, the cell or viral structural components or other polypeptides or nucleic acids commonly found associated with the polynucleotide.

Likewise, an "isolated" polypeptide means a polypeptide that is separated or substantially free from at least some of the other components of the naturally occurring organism or virus, for example, the cell or viral structural components or other polypeptides or nucleic acids commonly found associated with the polypeptide.

A "therapeutic polypeptide" is a polypeptide that may alleviate or reduce symptoms that result from an absence or defect in a protein in a cell or subject. Alternatively, a "therapeutic polypeptide" is one that otherwise confers a benefit to a subject, e.g., anti-cancer effects or improvement in transplant survivability.

As used herein, the term "modified," as applied to a polynucleotide or polypeptide sequence, refers to a sequence that differs from a wild-type sequence due to one or more deletions, additions, substitutions, or any combination thereof.

As used herein, by "isolate" or "purify" (or grammatical equivalents) a virus vector, it is meant that the virus vector is at least partially separated from at least some of the other components in the starting material.

By the terms "treat," "treating," or "treatment of" (and grammatical variations thereof) it is meant that the severity of the subject's condition is reduced, at least partially improved or stabilized and/or that some alleviation, mitigation, decrease or stabilization in at least one clinical symptom is achieved and/or there is a delay in the progression of the disease or disorder.

The terms "prevent," "preventing," and "prevention" (and grammatical variations thereof) refer to prevention and/or delay of the onset of a disease, disorder and/or a clinical symptom(s) in a subject and/or a reduction in the severity of the onset of the disease, disorder and/or clinical symptom(s) relative to what would occur in the absence of the methods of the invention. The prevention can be complete, e.g., the total absence of the disease, disorder and/or clinical symptom(s). The prevention can also be partial, such that the occurrence of the disease, disorder and/or clinical symptom(s) in the subject and/or the severity of onset is less than what would occur in the absence of the present invention.

A "treatment effective" amount as used herein is an amount that is sufficient to provide some improvement or benefit to the subject. Alternatively stated, a "treatment effective" amount is an amount that will provide some alleviation, mitigation, decrease or stabilization in at least one clinical symptom in the subject. Those skilled in the art will appreciate that the therapeutic effects need not be complete or curative, as long as some benefit is provided to the subject.

A "prevention effective" amount as used herein is an amount that is sufficient to prevent and/or delay the onset of a disease, disorder and/or clinical symptoms in a subject and/or to reduce and/or delay the severity of the onset of a disease, disorder and/or clinical symptoms in a subject relative to what would occur in the absence of the methods of the invention. Those skilled in the art will appreciate that the level of prevention need not be complete, as long as some benefit is provided to the subject.

The terms "heterologous nucleotide sequence" and "heterologous nucleic acid" are used interchangeably herein and refer to a sequence that is not naturally occurring in the virus. In some embodiments, the heterologous nucleic acid comprises an open reading frame that encodes a polypeptide or nontranslated RNA of interest (e.g., for delivery to a cell or subject).

As used herein, the terms "virus vector," "vector" or "gene delivery vector" refer to a virus (e.g., AAV) particle that functions as a nucleic acid delivery vehicle, and which comprises the vector genome (e.g., viral DNA [vDNA]) packaged within a virion. Alternatively, in some contexts, the term "vector" may be used to refer to the vector genome/vDNA alone or a plasmid.

The virus vectors of the invention can further be duplexed parvovirus particles as described in international patent publication WO 01/92551 (the disclosure of which is incorporated herein by reference in its entirety). Thus, in some embodiments, double stranded (duplex) genomes can be packaged.

A "rAAV vector genome" or "rAAV genome" is an AAV genome (i.e., vDNA) that comprises one or more heterologous nucleic acid sequences. rAAV vectors generally require only the 145 base ITR in cis to generate virus. All other viral sequences are dispensable and may be supplied in trans (Muzyczka (1992) Curr. Topics Microbiol. Immunol. 158: 97). Typically, the rAAV vector genome will only retain the one or more ITR sequence so as to maximize the size of the transgene that can be efficiently packaged by the vector. The structural and non-structural protein coding sequences may be provided in trans (e.g., from a vector, such as a plasmid, or by stably integrating the sequences into a packaging cell). In embodiments of the invention the rAAV vector genome comprises at least one ITR sequence (e.g., AAV ITR sequence), optionally two ITRs (e.g., two AAV ITRs), which typically will be at the 5' and 3' ends of the vector genome and flank the heterologous nucleic acid, but need not be contiguous thereto. The ITRs can be the same or different from each other.

The term "terminal repeat" or "TR" includes any viral terminal repeat or synthetic sequence that forms a hairpin structure and functions as an inverted terminal repeat (i.e., mediates the desired functions such as replication, virus packaging, integration and/or provirus rescue, and the like). The ITR can be an AAV ITR or a non-AAV ITR. For example, a non-AAV ITR sequence such as those of other parvoviruses (e.g., canine parvovirus, bovine parvovirus, mouse parvovirus, porcine parvovirus, human parvovirus B-19) or the SV40 hairpin that serves as the origin of SV40 replication can be used as an ITR, which can further be modified by truncation, substitution, deletion, insertion and/ or addition. Further, the ITR can be partially or completely synthetic, such as the "double-D sequence" as described in U.S. Pat. No. 5,478,745 to Samulski et al.

Parvovirus genomes have palindromic sequences at both their 5' and 3' ends. The palindromic nature of the sequences leads to the formation of a hairpin structure that is stabilized by the formation of hydrogen bonds between the complementary base pairs. This hairpin structure is believed to adopt a "Y" or a "T" shape. See, e.g., FIELDS et al., VIROLOGY, volume 2, chapters 69 & 70 (4th ed., Lippincott-Raven Publishers).

An "AAV inverted terminal repeat" or "AAV ITR" may be from any AAV, including but not limited to serotypes 1, 2, 3a, 3b, 4, 5, 6, 7, 8, 9, 10, 11, or 13, snake AAV, avian AAV, bovine AAV, canine AAV, equine AAV, ovine AAV, goat AAV, shrimp AAV, or any other AAV now known or later discovered (see, e.g., Table 1). An AAV ITR need not have the native terminal repeat sequence (e.g., a native AAV ITR sequence may be altered by insertion, deletion, truncation and/or missense mutations), as long as the terminal repeat mediates the desired functions, e.g., replication, virus packaging, persistence, and/or provirus rescue, and the like.

The virus vectors of the invention can further be "targeted" virus vectors (e.g., having a directed tropism) and/or a "hybrid" parvovirus (i.e., in which the viral ITRs and viral capsid are from different parvoviruses) as described in international patent publication WO 00/28004 and Chao et al., (2000) Mol. Therapy 2:619.

Further, the viral capsid or genomic elements can contain other modifications, including insertions, deletions and/or substitutions.

As used herein, the term "amino acid" encompasses any naturally occurring amino acids, modified forms thereof, and synthetic amino acids.

Naturally occurring, levorotatory (L-) amino acids are shown in Table 2.

TABLE 2

| Amino Acid Residue | Abbreviation | |
|---|---|---|
| | Three-Letter Code | One-Letter Code |
| Alanine | Ala | A |
| Arginine | Arg | R |
| Asparagine | Asn | N |
| Aspartic acid (Aspartate) | Asp | D |
| Cysteine | Cys | C |
| Glutamine | Gln | Q |
| Glutamic acid (Glutamate) | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Alternatively, the amino acid can be a modified amino acid residue (nonlimiting examples are shown in Table 3) or can be an amino acid that is modified by post-translation modification (e.g., acetylation, amidation, formylation, hydroxylation, methylation, phosphorylation or sulfatation).

TABLE 3

| Amino Acid Residue Derivatives | |
|---|---|
| Modified Amino Acid Residue | Abbreviation |
| 2-Aminoadipic acid | Aad |
| 3-Aminoadipic acid | bAad |
| beta-Alanine, beta-Aminoproprionic acid | bAla |

TABLE 3-continued

| Amino Acid Residue Derivatives | |
|---|---|
| Modified Amino Acid Residue | Abbreviation |
| 2-Aminobutyric acid | Abu |
| 4-Aminobutyric acid, Piperidinic acid | 4Abu |
| 6-Aminocaproic acid | Acp |
| 2-Aminoheptanoic acid | Ahe |
| 2-Aminoisobutyric acid | Aib |
| 3-Aminoisobutyric acid | bAib |
| 2-Aminopimelic acid | Apm |
| t-butylalanine | t-BuA |
| Citrulline | Cit |
| Cyclohexylalanine | Cha |
| 2,4-Diaminobutyric acid | Dbu |
| Desmosine | Des |
| 2,2'-Diaminopimelic acid | Dpm |
| 2,3-Diaminoproprionic acid | Dpr |
| N-Ethylglycine | EtGly |
| N-Ethylasparagine | EtAsn |
| Homoarginine | hArg |
| Homocysteine | hCys |
| Homoserine | hSer |
| Hydroxylysine | Hyl |
| Allo-Hydroxylysine | aHyl |
| 3-Hydroxyproline | 3Hyp |
| 4-Hydroxyproline | 4Hyp |
| Isodesmosine | Ide |
| allo-Isoleucine | aIle |
| Methionine sulfoxide | MSO |
| N-Methylglycine, sarcosine | MeGly |
| N-Methylisoleucine | MeIle |
| 6-N-Methyllysine | MeLys |
| N-Methylvaline | MeVal |
| 2-Naphthylalanine | 2-Nal |
| Norvaline | Nva |
| Norleucine | Nle |
| Ornithine | Orn |
| 4-Chlorophenylalanine | Phe(4-Cl) |
| 2-Fluorophenylalanine | Phe(2-F) |
| 3-Fluorophenylalanine | Phe(3-F) |
| 4-Fluorophenylalanine | Phe(4-F) |
| Phenylglycine | Phg |
| Beta-2-thienylalanine | Thi |

Further, the non-naturally occurring amino acid can be an "unnatural" amino acid as described by Wang et al., (2006) Annu. Rev. Biophys. Biomol. Struct. 35:225-49. These unnatural amino acids can advantageously be used to chemically link molecules of interest to the AAV capsid protein.

The term "template" or "substrate" is used herein to refer to a polynucleotide sequence that may be replicated to produce the parvovirus viral DNA. For the purpose of vector production, the template will typically be embedded within a larger nucleotide sequence or construct, including but not limited to a plasmid, naked DNA vector, bacterial artificial chromosome (BAC), yeast artificial chromosome (YAC) or a viral vector (e.g., adenovirus, herpesvirus, Epstein-Barr Virus, AAV, baculoviral, retroviral vectors, and the like). Alternatively, the template may be stably incorporated into the chromosome of a packaging cell.

As used herein, parvovirus or AAV "Rep coding sequences" indicate the nucleic acid sequences that encode the parvoviral or AAV non-structural proteins that mediate viral replication and the production of new virus particles. The parvovirus and AAV replication genes and proteins have been described in, e.g., FIELDS et al., VIROLOGY, volume 2, chapters 69 & 70 (4th ed., Lippincott-Raven Publishers).

The "Rep coding sequences" need not encode all of the parvoviral or AAV Rep proteins. For example, with respect to AAV, the Rep coding sequences do not need to encode all four AAV Rep proteins (Rep78, Rep 68, Rep52 and Rep40), in fact, it is believed that AAV5 only expresses the spliced Rep68 and Rep40 proteins. In representative embodiments, the Rep coding sequences encode at least those replication proteins that are necessary for viral genome replication and packaging into new virions. The Rep coding sequences will generally encode at least one large Rep protein (i.e., Rep78/68) and one small Rep protein (i.e., Rep52/40). In particular embodiments, the Rep coding sequences encode the AAV Rep78 protein and the AAV Rep52 and/or Rep40 proteins. In other embodiments, the Rep coding sequences encode the Rep68 and the Rep52 and/or Rep40 proteins. In a still further embodiment, the Rep coding sequences encode the Rep68 and Rep52 proteins, Rep68 and Rep40 proteins, Rep78 and Rep52 proteins, or Rep78 and Rep40 proteins.

As used herein, the term "large Rep protein" refers to Rep68 and/or Rep78. Large Rep proteins of the claimed invention may be either wild-type or synthetic. A wild-type large Rep protein may be from any parvovirus or AAV, including but not limited to serotypes 1, 2, 3a, 3b, 4, 5, 6, 7, 8, 9, 10, 11, or 13, or any other AAV now known or later discovered (see, e.g., Table 1). A synthetic large Rep protein may be altered by insertion, deletion, truncation and/or missense mutations.

Those skilled in the art will further appreciate that it is not necessary that the replication proteins be encoded by the same polynucleotide. For example, for MVM, the NS-1 and NS-2 proteins (which are splice variants) may be expressed independently of one another. Likewise, for AAV, the p19 promoter may be inactivated and the large Rep protein(s) expressed from one polynucleotide and the small Rep protein(s) expressed from a different polynucleotide. Typically, however, it will be more convenient to express the replication proteins from a single construct. In some systems, the viral promoters (e.g., AAV p19 promoter) may not be recognized by the cell, and it is therefore necessary to express the large and small Rep proteins from separate expression cassettes. In other instances, it may be desirable to express the large Rep and small Rep proteins separately, i.e., under the control of separate transcriptional and/or translational control elements. For example, it may be desirable to control expression of the large Rep proteins, so as to decrease the ratio of large to small Rep proteins. In the case of insect cells, it may be advantageous to down-regulate expression of the large Rep proteins (e.g., Rep78/68) to avoid toxicity to the cells (see, e.g., Urabe et al., (2002) *Human Gene Therapy* 13:1935).

As used herein, the parvovirus or AAV "cap coding sequences" encode the structural proteins that form a functional parvovirus or AAV capsid (i.e., can package DNA and infect target cells). Typically, the cap coding sequences will encode all of the parvovirus or AAV capsid subunits, but less than all of the capsid subunits may be encoded as long as a functional capsid is produced. Typically, but not necessarily, the cap coding sequences will be present on a single nucleic acid molecule.

The capsid structure of autonomous parvoviruses and AAV are described in more detail in BERNARD N. FIELDS et al., VIROLOGY, volume 2, chapters 69 & 70 (4th ed., Lippincott-Raven Publishers).

Parvovirus Vectors Expressing IDUA

The present invention provides parvovirus vectors, e.g., AAV vectors, that comprise a nucleotide sequence encoding IDUA and are capable of expressing IDUA in the cornea of a subject.

One aspect of the invention relates to a recombinant nucleic acid comprising, consisting essentially of, or consisting of a nucleotide sequence encoding human alpha-L-iduronidase (IDUA), wherein the nucleotide sequence has been codon-optimized for expression in human cells. In certain embodiments, the nucleic acid is a non-naturally occurring sequence. In some embodiments, the nucleic acid comprises, consists essentially of, or consists of a nucleotide sequence that is at least 90% identical to SEQ ID NO:1, e.g., at least 91%, 92%, 93%, 94%, 95%, 96%, 97%, 98%, or 99% identical to SEQ ID NO:1. In some embodiments, the nucleic acid comprises, consists essentially of, or consists of the nucleotide sequence of SEQ ID NO:1. In some embodiments, the nucleic acid comprises at least 10 contiguous nucleotides of SEQ ID NO:1, e.g., at least 10, 25, 50, 100, 200, 300, 400, 500, 600, 700, 800, 900, 1000, 1100, 1200, 1300, 1400, 1500, 1600, 1700, 1800 or more.

SEQ ID NO: 1

```
  1 CACCGGTCGC CACCATGCGA CCACTGAGAC CACGGGCCGC TCTGCTGGCT

51 CTGCTGGCTT CACTGCTGGC CGCTCCCCCT GTCGCTCCTG CTGAGGCTCC

101 CCACCTGGTG CATGTGGACG CAGCTCGCGC CCTGTGGCCA CTGAGGAGAT

151 TCTGGAGGAG CACAGGCTTT TGCCCACCTC TGCCTCACAG CCAGGCTGAC

201 CAGTACGTGC TGTCCTGGGA TCAGCAGCTG AACCTGGCAT ATGTGGGAGC

251 CGTCCCCCAC AGGGGGATCA AACAGGTGAG AACTCATTGG CTGCTGGAGC

301 TGGTCACCAC ACGAGGATCT ACTGGAAGGG GGCTGAGTTA CAACTTCACC

351 CACCTGGACG GCTATCTGGA TCTGCTGAGA GAGAATCAGC TGCTGCCTGG

401 ATTTGAACTG ATGGGCTCAG CCAGCGGACA TTTCACCGAC TTTGAGGATA

451 AGCAGCAGGT GTTCGAATGG AAAGACCTGG TCAGCTCCCT GGCTCGGCGC

501 TACATTGGGC GGTATGGCCT GGCACACGTG AGTAAGTGGA ACTTTGAGAC

551 TTGGAATGAA CCAGACCACC ATGACTTCGA TAACGTGTCA ATGACCATGC

601 AGGGGTTTCT GAATTACTAT GATGCCTGCT CCGAGGGCCT GCGGGCAGCC

651 TCTCCAGCTC TGCGACTGGG AGGACCAGGC GATTCCTTCC ACACACCACC
```

```
                           -continued
 701 CAGAAGTCCC CTGTCATGGG GCCTGCTGCG GCACTGTCAT GACGGAACCA

751 ACTTCTTTAC AGGAGAAGCA GGGGTGAGAC TGGATTACAT CTCCCTGCAT

801 CGAAAGGGGG CCAGGTCTAG TATCTCTATT CTGGAGCAGG AAAAGGTGGT

851 CGCTCAGCAG ATCCGGCAGC TGTTCCCCAA ATTTGCCGAC ACACCTATCT

901 ACAATGACGA GGCTGATCCT CTGGTGGGAT GGTCTCTGCC TCAGCCATGG

951 CGAGCCGATG TGACTTATGC TGCAATGGTG GTCAAAGTCA TTGCTCAGCA

1001 CCAGAACCTG CTGCTGGCAA ATACTACCAG TGCTTTCCCA TACGCACTGC

1051 TGAGTAACGA CAATGCCTTC CTGTCATATC ACCCCCATCC TTTTGCCCAG

1101 AGAACACTGA CTGCTCGGTT TCAGGTGAAC AATACCCGAC CTCCACATGT

1151 GCAGCTGCTG AGGAAGCCTG TCCTGACAGC CATGGGCCTG CTGGCTCTGC

1201 TGGACGAGGA ACAGCTGTGG GCAGAGGTGT CTCAGGCCGG GACTGTCCTG

1251 GATAGTAACC ACACCGTGGG CGTCCTGGCT TCTGCACATC GACCTCAGGG

1301 ACCAGCAGAC GCTTGGCGAG CAGCTGTGCT GATCTACGCA TCAGACGATA

1351 CACGAGCACA CCCTAACCGA AGCGTGGCAG TCACTCTGCG ACTGCGAGGA

1401 GTGCCACCTG GACCAGGACT GGTGTACGTC ACCCGCTATC TGGACAATGG

1451 CCTGTGCTCT CCCGATGGAG AGTGGCGAAG GCTGGGGAGG CCCGTGTTCC

1501 CTACAGCAGA GCAGTTTAGA CGGATGAGAG CAGCCGAAGA TCCAGTGGCT

1551 GCAGCACCAC GACCACTGCC TGCAGGAGGC AGACTGACCC TGCGGCCAGC

1601 CCTGCGCCTG CCAAGCCTGC TGCTGGTGCA CGTCTGCGCA AGGCCTGAAA

1651 AGCCACCCGG ACAGGTGACA AGGCTGAGAG CTCTGCCACT GACTCAGGGA

1701 CAGCTGGTGC TGGTCTGGTC AGACGAGCAT GTGGGGAGCA AATGTCTGTG

1751 GACTTACGAA ATTCAGTTCA GCCAGGATGG GAAGGCCTAT ACCCCTGTGA

1801 GCCGGAAACC CAGCACCTTC AACCTGTTCG TCTTTTCCCC AGACACCGGG

1851 GCCGTGTCCG GCTCTTACCG GGTCCGCGCT CTGGACTATT GGGCAAGGCC

1901 AGGCCCCTTC AGCGATCCTG TGCCATACCT GGAAGTGCCT GTGCCTCGCG

1951 GCCCACCATC TCCTGGAAAC CCTTGAGGGG ATCCGTCGAC TAG
```

Methods of codon optimizing a nucleotide sequence to maximize expression in an organism are well known in the art and can be carried out using software available to the public. The wild-type sequence of human IDUA is known in the art and can be found in databases such as GenBank. Examples of human IDUA accession numbers include A26494, AK291816, and AH002600, incorporated by reference herein in their entirety.

The invention also provides a viral vector genome comprising the IDUA nucleic acid of the invention. In certain embodiments, the IDUA nucleic acid is the wild-type human IDUA sequence or the codon-optimized sequence. The viral vector genome may be a parvovirus vector genome, e.g., an AAV vector genome. The viral vector may further comprise a promoter operably linked to the IDUA nucleic acid. In some embodiments, the promoter may be a constitutive promoter, e.g., a CMV promoter. In other embodiments, the promoter may be a tissue-specific or preferred promoter. The invention further provides a cell in vitro comprising the AAV vector genome of the invention, e.g., stably incorporated into the genome of the cell. The invention further provides a recombinant parvovirus particle (e.g., a recombinant AAV particle) comprising the viral vector genome of the invention. Viral vectors and viral particles are discussed further below.

In certain embodiments, the viral vector exhibits a modified tropism due to the presence of the capsid protein of the invention. In one embodiment, the parvovirus vector exhibits systemic tropism for the cornea. In other embodiments, the parvovirus vector has reduced tropism for liver compared to a virus vector comprising a wild-type capsid protein.

Methods of Producing Virus Vectors

The present invention further provides methods of producing virus vectors. In one particular embodiment, the present invention provides a method of producing a recombinant parvovirus particle, comprising providing to a cell permissive for parvovirus replication: (a) a recombinant parvovirus template comprising (i) a nucleic acid encoding IDUA, and (ii) a parvovirus ITR; (b) a polynucleotide comprising Rep and Cap coding sequences; under conditions sufficient for the replication and packaging of the recombinant parvovirus template; whereby recombinant parvovirus particles are produced in the cell. Conditions sufficient for the replication and packaging of the recombinant parvovirus template can be, e.g., the presence of AAV sequences sufficient for replication of the parvovirus template and encapsidation into parvovirus capsids (e.g., parvovirus rep sequences and parvovirus cap sequences) and helper sequences from adenovirus and/or herpesvirus. In particular embodiments, the parvovirus template comprises two parvovirus ITR sequences, which are located 5' and 3' to the heterologous nucleic acid sequence, although they need not be directly contiguous thereto.

In some embodiments, the recombinant parvovirus template comprises an ITR that is not resolved by Rep to make duplexed AAV vectors as described in international patent publication WO 01/92551.

The parvovirus template and parvovirus rep and cap sequences are provided under conditions such that virus vector comprising the parvovirus template packaged within the parvovirus capsid is produced in the cell. The method can further comprise the step of collecting the virus vector from the cell. The virus vector can be collected from the medium and/or by lysing the cells.

The cell can be a cell that is permissive for parvoviral viral replication. Any suitable cell known in the art may be employed. In particular embodiments, the cell is a mammalian cell (e.g., a primate or human cell). As another option, the cell can be a trans-complementing packaging cell line that provide functions deleted from a replication-defective helper virus, e.g., 293 cells or other E1a trans-complementing cells.

The parvovirus replication and capsid sequences may be provided by any method known in the art. Current protocols typically express the parvovirus rep/cap genes on a single plasmid. The parvovirus replication and packaging sequences need not be provided together, although it may be convenient to do so. The parvovirus rep and/or cap sequences may be provided by any viral or non-viral vector. For example, the rep/cap sequences may be provided by a hybrid adenovirus or herpesvirus vector (e.g., inserted into the E1a or E3 regions of a deleted adenovirus vector). EBV vectors may also be employed to express the parvovirus cap and rep genes. One advantage of this method is that EBV vectors are episomal, yet will maintain a high copy number throughout successive cell divisions (i.e., are stably integrated into the cell as extra-chromosomal elements, designated as an "EBV based nuclear episome," see Margolski, (1992) *Curr. Top. Microbiol. Immun.* 158:67).

As a further alternative, the rep/cap sequences may be stably incorporated into a cell.

Typically the parvovirus rep/cap sequences will not be flanked by the TRs, to prevent rescue and/or packaging of these sequences.

The parvovirus template can be provided to the cell using any method known in the art. For example, the template can be supplied by a non-viral (e.g., plasmid) or viral vector. In particular embodiments, the parvovirus template is supplied by a herpesvirus or adenovirus vector (e.g., inserted into the E1a or E3 regions of a deleted adenovirus). As another illustration, Palombo et al., (1998) *J. Virology* 72:5025, describes a baculovirus vector carrying a reporter gene flanked by the AAV TRs. EBV vectors may also be employed to deliver the template, as described above with respect to the rep/cap genes.

In another representative embodiment, the parvovirus template is provided by a replicating rAAV virus. In still other embodiments, an AAV provirus comprising the parvovirus template is stably integrated into the chromosome of the cell.

To enhance virus titers, helper virus functions (e.g., adenovirus or herpesvirus) that promote a productive parvovirus infection can be provided to the cell. Helper virus sequences necessary for parvovirus replication are known in the art. Typically, these sequences will be provided by a helper adenovirus or herpesvirus vector. Alternatively, the adenovirus or herpesvirus sequences can be provided by another non-viral or viral vector, e.g., as a non-infectious adenovirus miniplasmid that carries all of the helper genes that promote efficient parvovirus production as described by Ferrari et al., (1997) *Nature Med.* 3:1295, and U.S. Pat. Nos. 6,040,183 and 6,093,570.

Further, the helper virus functions may be provided by a packaging cell with the helper sequences embedded in the chromosome or maintained as a stable extrachromosomal element. Generally, the helper virus sequences cannot be packaged into AAV virions, e.g., are not flanked by ITRs.

Those skilled in the art will appreciate that it may be advantageous to provide the parvovirus replication and capsid sequences and the helper virus sequences (e.g., adenovirus sequences) on a single helper construct. This helper construct may be a non-viral or viral construct. As one nonlimiting illustration, the helper construct can be a hybrid adenovirus or hybrid herpesvirus comprising the AAV rep/cap genes.

In one particular embodiment, the parvovirus rep/cap sequences and the adenovirus helper sequences are supplied by a single adenovirus helper vector. This vector can further comprise the parvovirus template. The parvovirus rep/cap sequences and/or the parvovirus template can be inserted into a deleted region (e.g., the E1a or E3 regions) of the adenovirus.

In a further embodiment, the parvovirus rep/cap sequences and the adenovirus helper sequences are supplied by a single adenovirus helper vector. According to this embodiment, the parvovirus template can be provided as a plasmid template.

In another illustrative embodiment, the parvovirus rep/cap sequences and adenovirus helper sequences are provided by a single adenovirus helper vector, and the parvovirus template is integrated into the cell as a provirus. Alternatively, the parvovirus template is provided by an EBV vector that is maintained within the cell as an extrachromosomal element (e.g., as an EBV based nuclear episome).

In a further exemplary embodiment, the parvovirus rep/cap sequences and adenovirus helper sequences are provided by a single adenovirus helper. The parvovirus template can be provided as a separate replicating viral vector. For example, the parvovirus template can be provided by a parvovirus particle or a second recombinant adenovirus particle.

According to the foregoing methods, the hybrid adenovirus vector typically comprises the adenovirus 5' and 3' cis sequences sufficient for adenovirus replication and packaging (i.e., the adenovirus terminal repeats and PAC sequence). The parvovirus rep/cap sequences and, if present, the AAV template are embedded in the adenovirus backbone and are flanked by the 5' and 3' cis sequences, so that these sequences may be packaged into adenovirus capsids. As described above, the adenovirus helper sequences and the parvovirus rep/cap sequences are generally not flanked by ITRs so that these sequences are not packaged into the parvovirus virions.

Zhang et al., ((2001) *Gene Ther.* 18:704-12) describe a chimeric helper comprising both adenovirus and the AAV rep and cap genes.

Herpesvirus may also be used as a helper virus in parvovirus packaging methods. Hybrid herpesviruses encoding the parvovirus Rep protein(s) may advantageously facilitate scalable parvovirus vector production schemes. A hybrid herpes simplex virus type I (HSV-1) vector expressing the AAV-2 rep and cap genes has been described (Conway et al., (1999) *Gene Ther.* 6:986 and WO 00/17377.

As a further alternative, the virus vectors of the invention can be produced in insect cells using baculovirus vectors to deliver the rep/cap genes and parvovirus template as described, for example, by Urabe et al., (2002) *Human Gene Ther.* 13:1935-43.

Parvovirus vector stocks free of contaminating helper virus may be obtained by any method known in the art. For example, parvovirus and helper virus may be readily differentiated based on size. Parvovirus may also be separated away from helper virus based on affinity for a heparin substrate (Zolotukhin et al., (1999) *Gene Therapy* 6:973). Deleted replication-defective helper viruses can be used so that any contaminating helper virus is not replication competent. As a further alternative, an adenovirus helper lacking late gene expression may be employed, as only adenovirus early gene expression is required to mediate packaging of parvovirus. Adenovirus mutants defective for late gene expression are known in the art (e.g., ts100K and ts149 adenovirus mutants).

Recombinant Virus Vectors

The virus vectors of the present invention are useful for the delivery of nucleic acids to cells in vitro, ex vivo, and in vivo. In particular, the virus vectors can be advantageously employed to deliver or transfer nucleic acids to animal, including mammalian, cells. In particular, the virus vectors of the present invention are useful for the delivery of a nucleic acid encoding IDUA to the cornea of a subject.

Cornea targeted AAV gene therapy has been investigated in animal models primarily following two routes of administration; topical applications in wound healing assays and direct injection to the corneal stroma. Regarding topical applications, AAV serotype 9 (AAV9) was reported most efficient for stromal transduction, however, this was nearly entirely localized to the epithelial/stromal boundary (Sharma et al., *Exp. Eye Res.* 91(3):440 (2010)). Regarding AAV gene delivery following intrastromal injection into human cornea explants, it was observed that AAV8 was more efficient than AAV2 or AAV1 for stromal transduction, which encompassed multiple cell types including CD34$^+$ keratocytes and macrophages (Hippert et al., *PLoS One,* 7(4):e35318 (2012)). Importantly, both of these routes of drug administration observed no deleterious consequences related to the AAV vector (Sharma et al., *Exp. Eye Res.* 91(3):440 (2010); Hippert et al., *PLoS One,* 7(4):e35318 (2012); Mohan et al., *PLoS One* 6(10):e26432 (2011)).

It will be understood by those skilled in the art that the nucleic acid encoding IDUA can be operably associated with appropriate control sequences. For example, the nucleic acid can be operably associated with expression control elements, such as transcription/translation control signals, origins of replication, polyadenylation signals, internal ribosome entry sites (IRES), promoters, and/or enhancers, and the like.

Those skilled in the art will appreciate that a variety of promoter/enhancer elements can be used depending on the level and tissue-specific expression desired. The promoter/enhancer can be constitutive or inducible, depending on the pattern of expression desired. The promoter/enhancer can be native or foreign and can be a natural or a synthetic sequence. By foreign, it is intended that the transcriptional initiation region is not found in the wild-type host into which the transcriptional initiation region is introduced.

In particular embodiments, the promoter/enhancer elements can be native to the target cell or subject to be treated. In representative embodiments, the promoters/enhancer element can be native to the IDUA nucleic acid sequence. The promoter/enhancer element is generally chosen so that it functions in the target cell(s) of interest. Further, in particular embodiments the promoter/enhancer element is a mammalian promoter/enhancer element. The promoter/enhancer element may be constitutive or inducible.

Inducible expression control elements are typically advantageous in those applications in which it is desirable to provide regulation over expression of the nucleic acid sequence. Inducible promoters/enhancer elements for gene delivery can be tissue-specific or—preferred promoter/enhancer elements, and include eye specific or preferred (including retina-specific and cornea-specific) promoter/enhancer elements. Other inducible promoter/enhancer elements include hormone-inducible and metal-inducible elements. Exemplary inducible promoters/enhancer elements include, but are not limited to, a Tet on/off element, a RU486-inducible promoter, an ecdysone-inducible promoter, a rapamycin-inducible promoter, and a metallothionein promoter.

In embodiments wherein the nucleic acid sequence is transcribed and then translated in the target cells, specific initiation signals are generally included for efficient translation of inserted protein coding sequences. These exogenous translational control sequences, which may include the ATG initiation codon and adjacent sequences, can be of a variety of origins, both natural and synthetic.

The virus vectors of the invention can be parvovirus vectors, e.g., AAV vectors. The AAV vectors may be any AAV serotype. In some embodiments, the AAV vector is an AAV2, AAV8, or AAV9 vector. In some embodiments, the AAV vector is a hybrid vector, e.g., one having a capsid protein from one serotype and a genome from another serotype or one having a synthetic capsid protein. In certain embodiments, the vector comprises a hybrid capsid with an altered tropism. In one example the hybrid capsid comprising a glycan binding site (e.g., a galactose binding site) from one serotype (e.g., AAV9) in a capsid sequence from another serotype (e.g., AAV8) (see, e.g., WO 2014/144229, incorporated by reference herein in its entirety).

The virus vectors according to the present invention provide a means for delivering IDUA nucleic acids into a broad range of cells, including dividing and non-dividing cells. The virus vectors can be employed to deliver the nucleic acid to a cell in vitro, e.g., to produce a polypeptide in vitro or for ex vivo gene therapy. The virus vectors are additionally useful in a method of delivering the nucleic acid to a subject in need thereof, e.g., to express IDUA. In this manner, the polypeptide can be produced in vivo in the subject. The subject can be in need of the polypeptide because the subject has a deficiency of the polypeptide. Further, the method can be practiced because the production of the polypeptide in the subject may impart some beneficial effect.

The virus vectors can also be used to produce IDUA in cultured cells or in a subject (e.g., using the subject as a bioreactor to produce the polypeptide or to observe the effects of the polypeptide on the subject, for example, in connection with screening methods).

The virus vectors of the present invention can be employed to deliver a nucleic acid encoding IDUA to treat and/or prevent any disease state for which it is beneficial to deliver IDUA, e.g., MPS I.

Virus vectors according to the instant invention find use in diagnostic and screening methods, whereby the IDUA nucleic acid is transiently or stably expressed in a cell culture system, in an organ or organ culture (e.g., an eye), or alternatively, a transgenic animal model.

The virus vectors of the present invention can also be used for various non-therapeutic purposes, including but not limited to use in protocols to assess gene targeting, clearance, transcription, translation, etc., as would be apparent to one skilled in the art. The virus vectors can also be used for the purpose of evaluating safety (spread, toxicity, immunogenicity, etc.). Such data, for example, are considered by the United States Food and Drug Administration as part of the regulatory approval process prior to evaluation of clinical efficacy.

Alternatively, the virus vector may be administered to a cell ex vivo, e.g., a corneal explant, and the altered cell or explant is administered to the subject. The virus vector comprising the IDUA nucleic acid is introduced into the cell, and the cell is administered to the subject, where the nucleic acid can be expressed.

Subjects, Pharmaceutical Formulations, and Modes of Administration

Virus vectors and capsids according to the present invention find use in both veterinary and medical applications. Suitable subjects include both avians and mammals. The term "avian" as used herein includes, but is not limited to, chickens, ducks, geese, quail, turkeys, pheasant, parrots, parakeets, and the like. The term "mammal" as used herein includes, but is not limited to, humans, non-human primates, bovines, ovines, caprines, equines, felines, canines, lagomorphs, etc. Human subjects include neonates, infants, juveniles and adults.

In particular embodiments, the present invention provides a pharmaceutical composition comprising a virus vector of the invention in a pharmaceutically acceptable carrier and, optionally, other medicinal agents, pharmaceutical agents, stabilizing agents, buffers, carriers, adjuvants, diluents, etc. For injection, the carrier will typically be a liquid. For other methods of administration, the carrier may be either solid or liquid. For inhalation administration, the carrier will be respirable, and optionally can be in solid or liquid particulate form.

By "pharmaceutically acceptable" it is meant a material that is not toxic or otherwise undesirable, i.e., the material may be administered to a subject without causing any undesirable biological effects.

One aspect of the present invention is a method of transferring a nucleic acid to a cell in vitro. The virus vector may be introduced into the cells at the appropriate multiplicity of infection according to standard transduction methods suitable for the particular target cells. Titers of virus vector to administer can vary, depending upon the target cell type and number, and the particular virus vector, and can be determined by those of skill in the art without undue experimentation. In representative embodiments, at least about $10^3$ infectious units, more preferably at least about $10^5$ infectious units are introduced to the cell.

The cell(s) into which the virus vector is introduced can be of any type, including but not limited to cells of the eye (including retinal cells, retinal pigment epithelium, and corneal cells (e.g., keratocytes, epithelial cells, and endothelial cells). Moreover, the cell can be from any species of origin, as indicated above.

The virus vector can be introduced into cells in vitro for the purpose of administering the modified cell to a subject. In particular embodiments, the cells have been removed from a subject, the virus vector is introduced therein, and the cells are then administered back into the subject. Methods of removing cells from subject for manipulation ex vivo, followed by introduction back into the subject are known in the art (see, e.g., U.S. Pat. No. 5,399,346). Alternatively, the recombinant virus vector can be introduced into cells from a donor subject, into cultured cells, or into cells from any other suitable source, and the cells are administered to a subject in need thereof (i.e., a "recipient" subject).

Suitable cells for ex vivo gene delivery are as described above. Dosages of the cells to administer to a subject will vary upon the age, condition and species of the subject, the type of cell, the nucleic acid being expressed by the cell, the mode of administration, and the like. Typically, at least about $10^2$ to about $10^8$ cells or at least about $10^3$ to about $10^6$ cells will be administered per dose in a pharmaceutically acceptable carrier. In particular embodiments, the cells transduced with the virus vector are administered to the subject in a treatment effective or prevention effective amount in combination with a pharmaceutical carrier.

A further aspect of the invention is a method of administering the virus vector to subjects. Administration of the virus vectors according to the present invention to a human subject or an animal in need thereof can be by any means known in the art. Optionally, the virus vector is delivered in a treatment effective or prevention effective dose in a pharmaceutically acceptable carrier.

Dosages of the virus vector to be administered to a subject depend upon the mode of administration, the disease or condition to be treated and/or prevented, the individual subject's condition, the particular virus vector, and the nucleic acid to be delivered, and the like, and can be determined in a routine manner. Exemplary doses for achieving therapeutic effects are titers of at least about $10^5$, $10^6$, $10^7$, $10^8$, $10^9$, $10^{10}$, $10^{11}$, $10^{12}$, $10^{13}$, $10^{14}$, $10^{15}$ transducing units, optionally about $10^8$ to about $10^{13}$ transducing units.

In particular embodiments, more than one administration (e.g., two, three, four or more administrations) may be employed to achieve the desired level of gene expression over a period of various intervals, e.g., daily, weekly, monthly, yearly, etc.

Exemplary modes of administration to the cornea include intrastromal, topical, intravitreal, and subretinal.

Delivery to a target tissue can also be achieved by delivering a depot comprising the virus vector. In representative embodiments, a depot comprising the virus vector is implanted into the cornea or other tissue of the eye or the tissue can be contacted with a film or other matrix comprising the virus vector. Such implantable matrices or substrates are described in U.S. Pat. No. 7,201,898.

In particular embodiments, a virus vector according to the present invention is administered to the cornea to treat, delay the onset of and/or prevent corneal clouding and/or blindness associated with MPS I.

Thus, as one aspect, the invention further encompasses a method of delivering IDUA to the cornea of a subject, comprising administering to the cornea of the subject an effective amount of an AAV particle that expresses IDUA, thereby delivering IDUA to the cornea of the subject.

In another aspect, the invention further encompasses a method of treating, delaying the onset of, and/or preventing MPS I-associated corneal clouding in a subject in need thereof, comprising administering to the cornea of the subject a therapeutically effective amount of an AAV particle that expresses IDUA, thereby treating, delaying the onset of, and/or preventing MPS I-associated corneal clouding in the subject.

In a further aspect, the invention further encompasses a method of delivering IDUA to a cornea in vitro or ex vivo, e.g., prior to transplantation in a subject in need thereof, comprising contacting the cornea with an effective amount of an AAV particle that expresses IDUA, thereby delivering IDUA to the cornea. In some embodiments, the cornea may be incubated with the AAV particle or the AAV particle may be injected into the cornea.

In the methods of the invention, the subject may be one has been diagnosed with MPS I or is suspected of having MPS I. In certain embodiments, the subject is an infant or child, e.g., less than 18 years old, e.g., less than 18, 17, 16, 15, 14, 13, 12, 11, 10, 9, 8, 7, 6, or 5 years old. In some embodiments, the subject has not developed clouding of the cornea. In other embodiments, the subject has at least partial clouding of the cornea, e.g., the subject's eyesight has been reduced by less than about 10%, e.g., less than about 10%, 20%, 30%, 40%, 50%, 60%, 70%, 80%, or 90% relative to a subject that does not have MPS I.

Injectables can be prepared in conventional forms, either as liquid solutions or suspensions, solid forms suitable for solution or suspension in liquid prior to injection, or as emulsions. Alternatively, one may administer the virus vector and/or virus capsids of the invention in a local manner, for example, in a depot or sustained-release formulation. Further, the virus vector and/or virus capsid can be delivered adhered to a surgically implantable matrix (e.g., as described in U.S. Patent Publication No. 2004-0013645).

Having described the present invention, the same will be explained in greater detail in the following examples, which are included herein for illustration purposes only, and which are not intended to be limiting to the invention.

Example 1

Materials and Methods

Production of AAV Vectors. For cell culture experiments, a previously described triple transfection method was used to generate the vectors used herein (Grieger et al., *Nat. Protoc.* 1(3):1412 (2006)). This method used the pXR2 or pXR8G9 plasmids, which all contain rep2 of AAV and individually the capsid genes of the indicated serotype. The plasmid containing the intended AAV genome was first constructed by substituting the egfp gene in pTR-CMV-eGFP with the codon optimized IDUA cDNA (provided by GenScript) at the AgeI and SalI sites. Following AAV production and cesium chloride gradient separation (Grieger et al., *Nat. Protoc.* 1(3):1412 (2006)), peak fractions were dialyzed against PBS, and titered by quantitative PCR (CMV_F CAA GTA CGC CCC CTA TTG AC (SEQ ID NO:2), CMV_R AAG TCC CGT TGA TTT TGG TG (SEQ ID NO:3)) which was confirmed by Southern dot blot (Grieger et al., *Nat. Protoc.* 1(3):1412 (2006)). For the experiments in human explants, GMP grade vector preparations were provided by the UNC vector core.

Cell Culture and Vector Transduction: Human embryonic kidney 293 cells, MPS I patient fibroblasts, and normal human fibroblasts (Simpson et al., *J. Carcinog.* 4:18 (2005)) were maintained at 37° C. in a 5% $CO_2$ atmosphere in Dulbecco's modified Eagle's medium (Sigma) supplemented with 10% fetal bovine serum and penicillin-streptomycin (100 U/ml). Transduction of cultured cells was performed in a 24 well plate in a fixed volume. For these experiments, vector was added to the wells at the indicated viral genome per cell dose and was not removed for the duration of the experiment.

Human Cornea Experiments: All experimental protocols were approved by the University of North Carolina at Chapel Hill. Human corneas were provided by the miracles in sight tissue procurement bank. These deidentified postmortem tissue experiments were performed in accordance with the human subjects research office of human research ethics at the University of North Carolina at Chapel Hill (IRB-14-1019). The corneas of both genders were maintained in the supplied opti-mem at 37° C. in a 5% $CO_2$ atmosphere. Injections were performed with a 31 gauge insulin syringe. India ink was used as a dye to verify the injections. Corneas were then cultured for 7 days and analyzed as described in the text.

Functional IDUA Assay: Quantitative IDUA enzyme activities were measured as previously described (Garcia-Rivera et al., *Brain Res. Bull.* 74(6):429 (2007)). Briefly, 10 μl of a supernatant or cell lysis solution were incubated with 50 μM 4-methylumbelliferyl alpha-L-iduronide made in 0.4M sodium formate buffer, pH 3.5, containing 0.2% Triton x-100 at 37° C. for 60 min in the dark. Reactions were stopped by adding 80 μl of 0.5M NaOH/glycine buffer pH 10.3. The 96 well plates were centrifuged for 1 min 13000 rpm at 4° C. and supernatants were transferred to a black 96 well plate, clear bottom with lid for measuring fluorescence at 450 nm, following excitation at 365 nm. The amount of cleaved substrate was calculated from a standard curve, previously established with 4-methylumbelliferone and expressed as nmol/h/mg for enzyme activity in cell lysates, or nmol/h/10 μl for analysis of supernatants. The protein amount for each sample was determined with the BCA assay.

Tunel Assay: Apoptotic cells generated due to the cellular cytotoxicity during AAV transduction were determined by deoxynucleotidyltransferase (TdT)-mediated dUTP-biotin nick end labeling with DAB. Tunel assay was performed with TACS2 TdT-Blue Label in situ apoptosis detection kit (Trevigen, Gaithersburg, Md.). Briefly, following deparaffinization and rehydration, the human cornea sections were digested for 20 min in proteinase K. Slides were washed with 1×PBS and the endogenous peroxidase activity was quenched by incubating the tissues with 3% $H_2O_2$ solution in methanol. After washing the slides with 1×PBS, tissue sections were incubated with 1×TdT labeling buffer for 5 min. The labeling reaction consisting of incubating the cornea tissues with TdT enzyme, dNTPs with biotinylated dUTP, and 1×manganese chloride in 1×TdT labeling buffer for 1 h in a humidified chamber at 37 C. The reaction was completed by incubating with 1×TdT stop buffer. The fragmented DNA was visualized by treating the sections with streptavidin-conjugated horseradish peroxidase and DAB solution.

Immunofluorescence Staining: Human cornea tissues were embedded in paraffin and sectioned at a thickness of 5 μm using a microtome. In order to stain the slide with immunofluorescence antibodies, sections were deparaffinized by incubating the slides in xylene for 5 min, two times total, followed by rehydration by immersing them sequentially in 100%, 95% and 70% ethanol solutions, 5 min each, and finally in water for 5 min. Before staining the sections, antigen retrieval procedure was performed in order to guarantee the exposure of epitopes, which were previously masked due to the paraffin embedding process. Specifically, slides were immerse into pre-heated antigen retrieval solution (Dako) at 98° C. for 7 min. Non-specific binding sites within the tissues were then blocked by incubating the slides with 10% NGS, in 1×PBS for 1 hour at RT. Slides were washed twice for 5 minutes each with 2% NGS in 1×PBS. Sections were then incubated overnight at 4° C. with primary antibody diluted appropriately in a solution consisting of 2% NGS in 1×PBS. After incubation with primary antibody, slides were washed three times, for 5 minutes each, in order to remove non-specifically bound primary antibody. The washing solution contained 2% NGS in 1×PBS. An appropriate fluorescently-labeled secondary antibody (5 µg/ml) was then added to the slides diluted in 2% NGS in 1×PBS, and slides were incubated for 1 hour at 4° C. Finally, slides were washed twice with 2% NGS in 1×PBS three times, for five minutes each, followed by a last wash with 1×PBS at 4° C. A couple of drops of Hoechst (Molecular probes—Life technologies, H3569 Hoechst 33258, Pentahydrate—1 µg/mL) were added for 7 minutes to counterstain the nuclei within the section, followed by a wash with water. Slides were then coverslipped with Cytoseal 60 (Thermo Fisher Scientific (NYSE: TMO)).

Primary Antibodies Used for this Study were the Following: For IDUA staining, Rabbit Polyclonal IDUA antibody (Biorbyt, catalog number: orb157615, dilution 1/50); for GFP staining, Chicken anti GFP antibody (Ayes, catalog number: GFP-1020, dilution 1/100); for CD34 staining, mouse monoclonal antibody (clone: B-6) (Santa Cruz, sc-74499, dilution 1/100)), for α-Smooth Muscle Actin staining, mouse monoclonal antibody (R&D, clone #1A4, catalog number MAB1420, dilution 1/100), and for F4/80 marker staining, rat monoclonal antibody, (clone: BM8) (Santa Cruz, sc-52664, dilution 1/100). Secondary antibodies were the following: Alexa Fluor® 594 goat anti-rabbit IgG (A-11012) (Gibco-Invitrogen, Carlsbad, Calif.), Alexa Fluor® 594 goat anti-chicken IgG (A-11039) (Gibco-Invitrogen, Carlsbad, Calif.), Alexa Fluor® 594 goat anti-rat IgG (A-11006) (Gibco-Invitrogen, Carlsbad, Calif.) and Alexa Fluor® 488 goat anti-mouse IgG (A-11001) (Gibco-Invitrogen, Carlsbad, Calif.). Images from each slide were taken using a Zeiss LSM 780 Confocal Microscope with a 40× objective (Olympus, Tokyo, Japan). Images that comprised the complete human cornea were taken with 10× objective, the title function and then stitched. Images were then processed using Adobe Photoshop. Sections from each tissue were stained with secondary antibody alone as negative control staining in all experiments.

MPS I Cell Transfection and Western Blot: MPS I fibroblast patient cells were plated onto a 24 well plate at 20,000 cells per well. After 24 hours, nine wells were transfected for each treatment adding a mix 1 µg of plasmid DNA, 3 µl of PEI and 60 µl of DMEM to each well. 24 hours after transfection, 40 µl of supernatant were collected from each well and 3 wells were combined to form each sample. 40 µl of DMEM were added to each well to maintain the same volume for later supernatant collections. 48 hours after transfection, total supernatant was collected combining 3 wells to again form triplicates. At that time total cell protein was harvested by adding 70 µl of Mammalian Protein extraction Reagent (Thermo Scientific Cat: 78501), per well and following reagent protocol.

For Western blot, protein lysate was added to a solution of 5% beta-mercapto-ethanol in 4× Nupage sample buffer. The resulting solution was boiled for 10 minutes and chilled on ice for 10 minutes and then run in a 10% Bis-tris pre-cast gel. Gel was run in 1×MOPS running buffer, and transferred to a nitrocellulose membrane. The membrane was blocked with 5% milk in ddH20, and probed with mouse host IDUA antibody (R&D Systems MAB-4119) for 2 hours at 1:500 dilution in PBS-Tween solution (0.5% Tween 20 in 1×PBS) or mouse host beta-actin antibody (Sigma) at 1:5000 dilution in PBS-Tween. This was followed by mouse horse radish peroxidase secondary antibody at 1:10000 dilution in PBS-Tween. Western-Bright Sirius chemi-luminescence reagent was used according to product protocol and blots were exposed using autoradiography film.

293 Cell Transfection Comparison of Wild-Type Against Codon Optimized IDUA: 293 cells were plated onto a 24 well plate at 100,000 cells per well. After 24 hours, 3 wells were transfected using a mix of 1 µg of plasmid DNA, 3 µl of PEI and 60 µl of DMEM per well. Total cell protein was harvested after 72 hours by adding 70 µl of Mammalian Protein extraction Reagent (Thermo Scientific Cat: 78501), to each well after saving the cell culture supernatant.

MPS I Patient Cell Toxicity Assay: Patient cells were plated onto a 24 well plate at 20,000 cells per well. AAV-2 316 was added after 24 hours in quadruplicates. After 72 hours, supernatant was saved; cells were resuspended using 0.05% trypsin and their corresponding supernatant. All samples were analyzed using a Beckman Vi-cell XR cell viability analyzer.

Example 2

AAV IDUA Expression Cassette in MPS I Fibroblasts

Figure 1B:
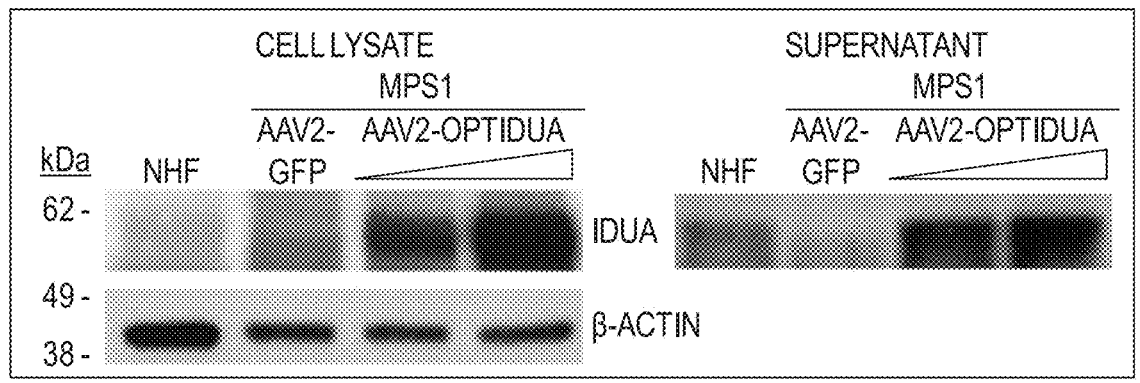
Figure 1C:
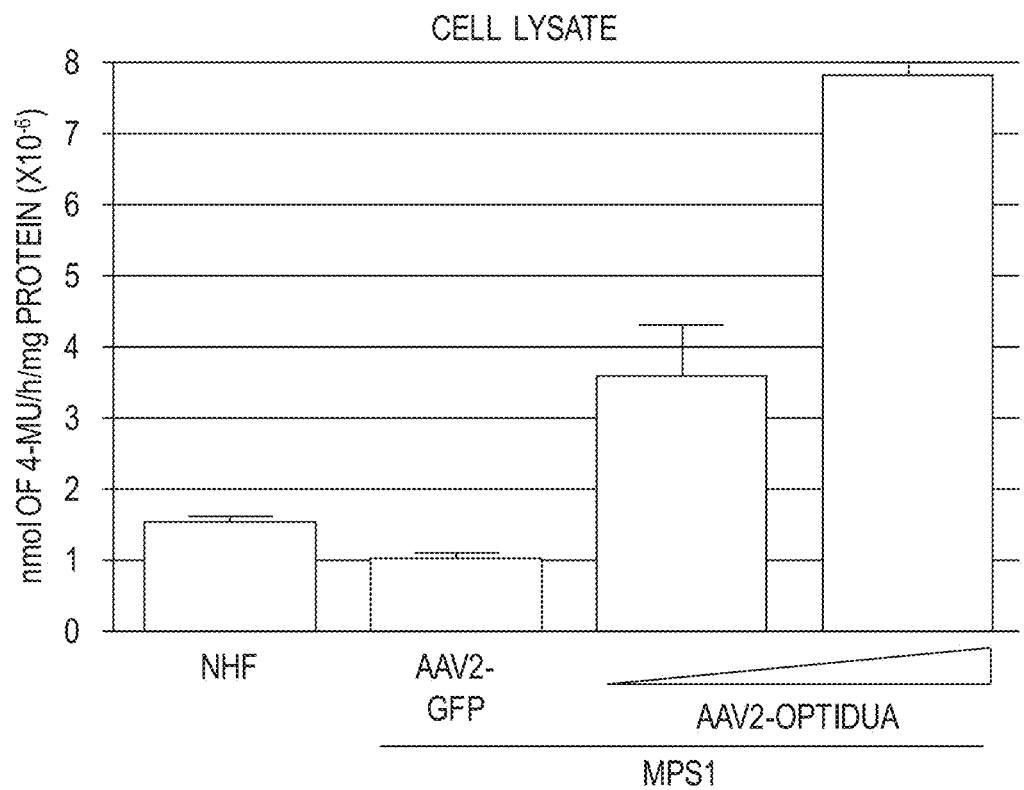
Figure 1D:
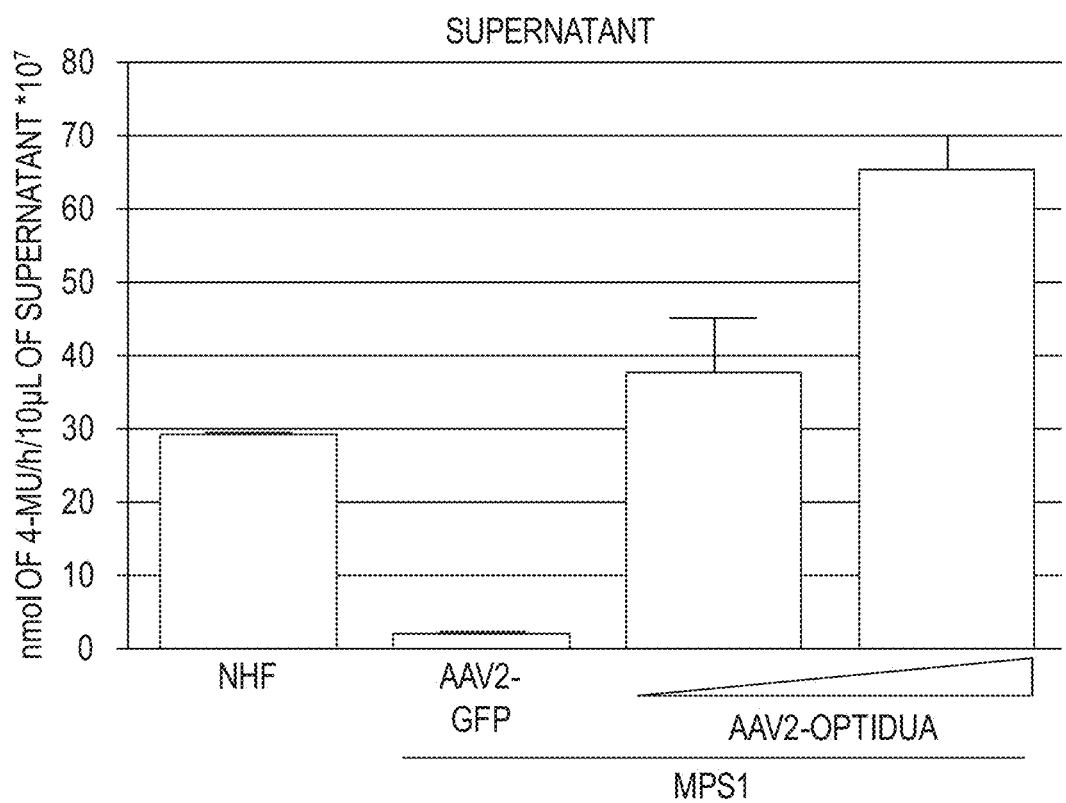
Figure 2:
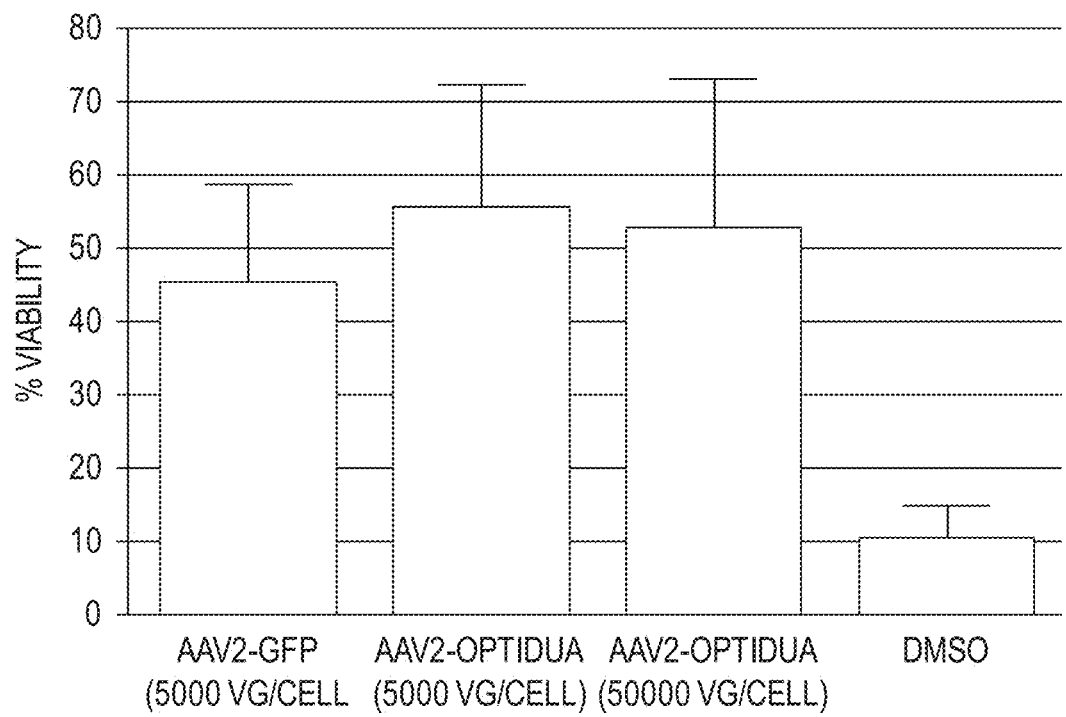
FIG. 2 shows no cytotoxicity following AAV2-GFP and AAV2-optIDUA administration to MPS I fibroblasts.

To develop an AAV IDUA expression cassette, the human idua cDNA (NM_000203) was codon optimized for human expression (opt-IDUA) and situated between the CMV promoter and the SV40 poly-adenylation sequence in an AAV inverted terminal repeat serotype 2 plasmid context (FIG. 1A). AAV2-opt-IDUA vectors were prepared as described (Grieger et al., Adv. Biochem. Eng. Biotechnol. 99:119 (2005)) and used for characterization in MPS I patient derived fibroblasts. Immortalized normal human fibroblasts (NHF) served as the control cell line (Simpson et al., J. Carcinog. 4:18 (2005)). In dose escalation experiments, AAV2-opt-IDUA transduction of MPS I fibroblasts resulted in increasing levels of IDUA restoration, in both cellular lysates and in the culture supernatant (FIG. 1B). In fact, as resting levels of IDUA in NHF are relatively low, a dose of 5,000 viral genomes/cell resulted in already supra-physiological levels in both cell lysates and in culture supernatants (FIG. 1B). Consistently, IDUA function was restored and elevated in transduced MPS I patient fibroblasts with a 10-fold and 30-fold increases in cellular lysate and supernatant, respectively, at the highest investigated dose (FIGS. 1C and 1D). Despite IDUA overproduction following AAV vector transduction, no toxicity was observed in patient fibroblasts at any dose using a dye exclusion assay (FIG. 2). Importantly, these results demonstrate the functionality and safety of AAV2-opt-IDUA in a MPS I patient context.

Example 3

AAV IDUA Expression Cassette in Corneas

Figure 3:
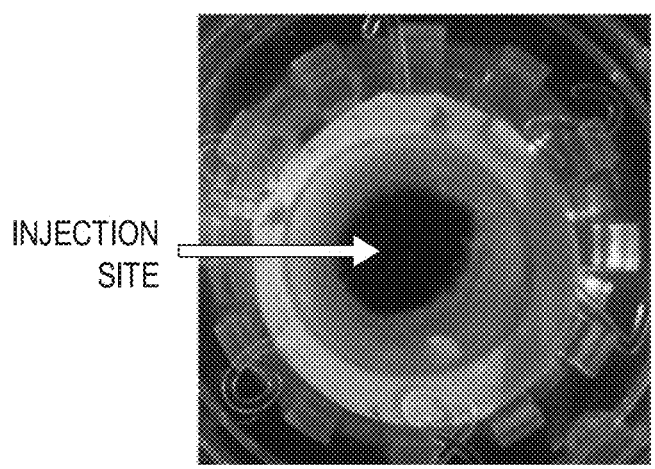
FIG. 3 shows the distribution of vehicle containing india ink after injection into the cornea.
Figure 4A:
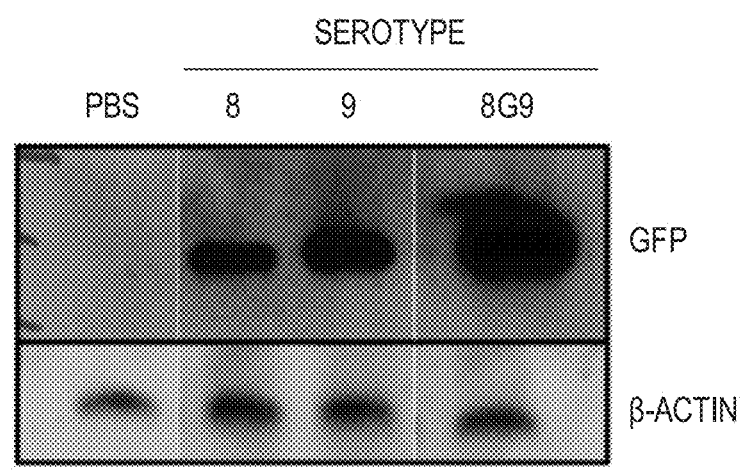
FIGS. 4A-4C show AAV capsid serotype evaluation in human cornea. (A) Human cornea stromas were injected with self-complementary CMV-GFP cassette encapsidated in AAV serotypes 8, 9, or the 8/9 chimeric 8G9. Seven days later Western blot was used to detect GFP. PBS corresponds to a human cornea injected with only PBS (vehicle control). Detection of β-actin was performed as a loading control. (B) Single-strand AAV8G9-CMV-GFP was injected into the stroma of human corneas and harvested for histology 7 days later. Left—Immunofluorescence image showing the distribution of recombinant AAV8G9-GFP viral infection across a human cornea section. Human corneas injected with PBS served as the negative control. Images were obtained with 10× objective and assembled by stitch processing. The scale bar is equal to 2000 μm. Right—Different areas of the same stained human cornea taken with 20× objective. The scale bar is equal to 100 μm. DAPI was used for nuclei counterstain. (C) A representative section of the corneas in (B) stained with GFP and the indicated cell marker. The scale bar is equal to 10 μm. DAPI was used for nuclei counterstain.

An analysis of MPS I patient corneas attributed stromal abnormalities as the cause of the corneal opacity that results in vision loss (Huang et al., *Exp. Eye Res.* 62(4):377 (1996)). Therefore, direct administration of AAV-opt-IDUA should restore IDUA activity in the corneal stroma compartment of MPS I patients, hopefully preventing or reversing the MPS I phenotype. Previous reports demonstrated the utility of both AAV8 (Hippert et al., *PLoS One,* 7(4):e35318 (2012)) and AAV9 (Sharma et al., *Exp. Eye Res.* 91(3):440 (2010)) for human keratocyte transduction, one of the most prevalent cell types present in the cornea. As such, these capsids, carrying a self-complementary (sc) AAV-CMV-GFP genome, were evaluated in normal human corneal explants, which remain viable for weeks post-mortem. Preliminary experiments demonstrated that a volume of 50 µl injected into the stroma was tolerated with minimal tissue distension and a distribution across of the adult cornea using the vector vehicle containing india ink (FIG. 3). Therefore, AAV serotypes 8 or 9 containing a GFP reporter gene were administered to human cornea stroma by injection ($1e^{10}$ vg in 50 µl) and analyzed seven days later by Western blotting. Given the reports of both 8 and 9 for cornea transduction, an AAV8/9 chimeric capsid (8G9), containing the galactose receptor of AAV9 engrafted on the AAV8 capsid was also investigated in the same manner (Sharma et al., *Exp. Eye Res.* 91(3):440 (2010); Hippert et al., *PLoS One,* 7(4): e35318 (2012)). Western blotting demonstrated that AAV8G9-GFP resulted in greater transduction than either parent serotype (FIG. 4A).

Figure 4B:
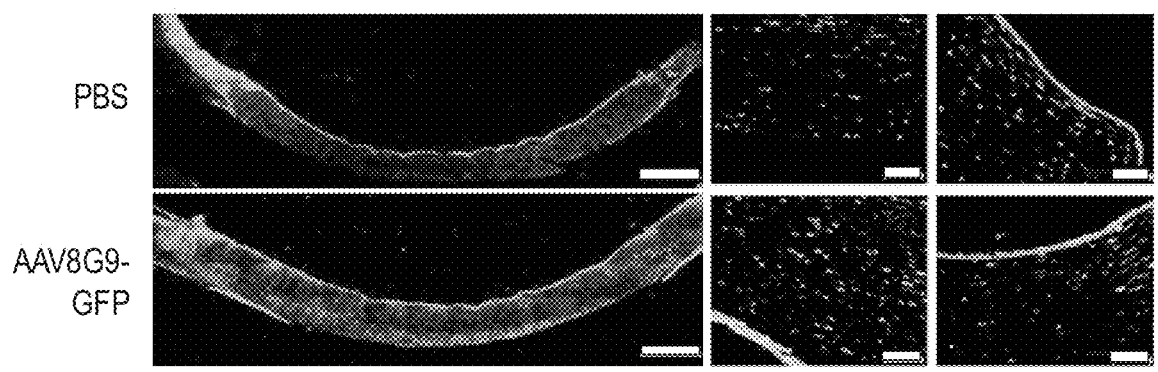
Figure 4C:
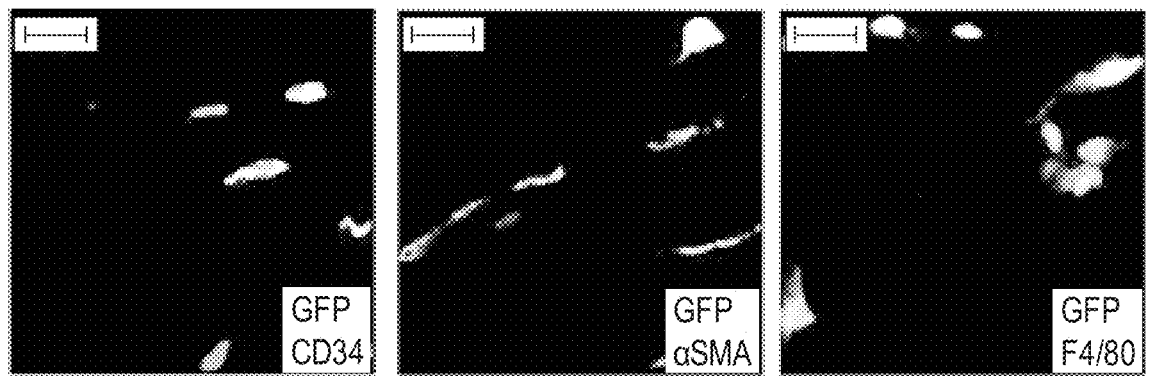

In order to determine the biodistribution of single-strand AAV8G9-GFP transduction (final volume 50 µl), GFP immunofluorescence was performed on human corneal cross sections. The results demonstrate a lateral spread of vector transduction across the cornea with penetration into the deeper stromal layers, including some endothelial cell transduction (FIG. 4B). Co-staining with CD34, a marker of keratocytes, with alpha-smooth muscle actin (alpha-SM), indicative of differentiated keratocytes, and with F4/80, a macrophage marker, demonstrated the corneal cell promiscuity for the AAV8G9 capsid (FIG. 4C).

Figure 5A:
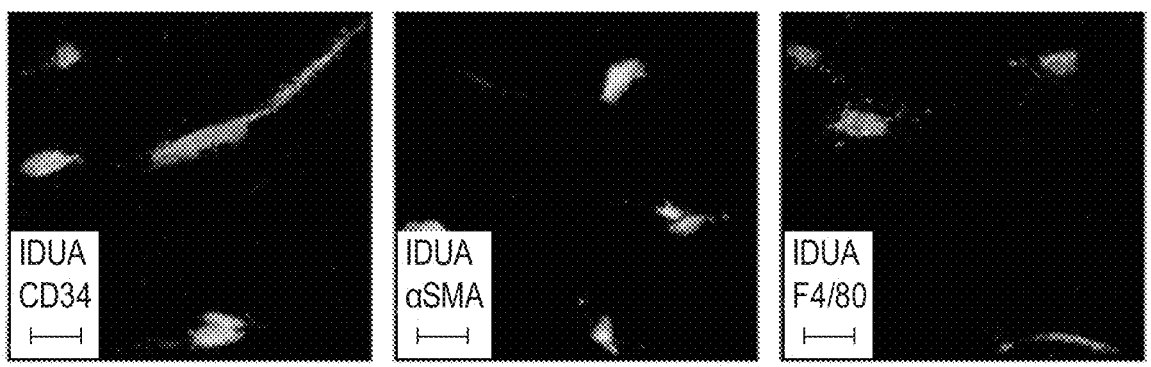
FIGS. 5A-5C show restoration of IDUA activity in human corneas by AAV8G9-opt-IDUA. (A) A representative section of a normal non-injected cornea stained with IDUA antibody and a cell marker. DAPI was used for nuclei counterstain. The scale bar is equal to 10 μm. (B) Western blot detecting IDUA amounts produced after injection of AAV8G9-IDUA. Administration of AAV8G9-GFP served as a vector infection control. B-actin serves as a loading control. (C) Functional activity of IDUA protein obtained from human corneas 7 days post-injection of AAV8G9-opt-IDUA. AAV8G9-GFP served as the negative control. The nmoles of 4-MU were normalized to one hour reaction and mg total protein. PBS corresponds to a human cornea injected with only the vehicle control.

Following confirmation that the AAV8G9 capsid was the most efficient for corneal stroma transduction, it was determined if the cell types transduced by AAV8G9 naturally produce IDUA. To do this, dual staining for the cell type marker and the IDUA protein was performed in normal untreated human corneas. The results indicate that all of the confirmed corneal cell types transduced by AAV8G9 naturally produce IDUA (FIG. 5A).

Figure 5B:
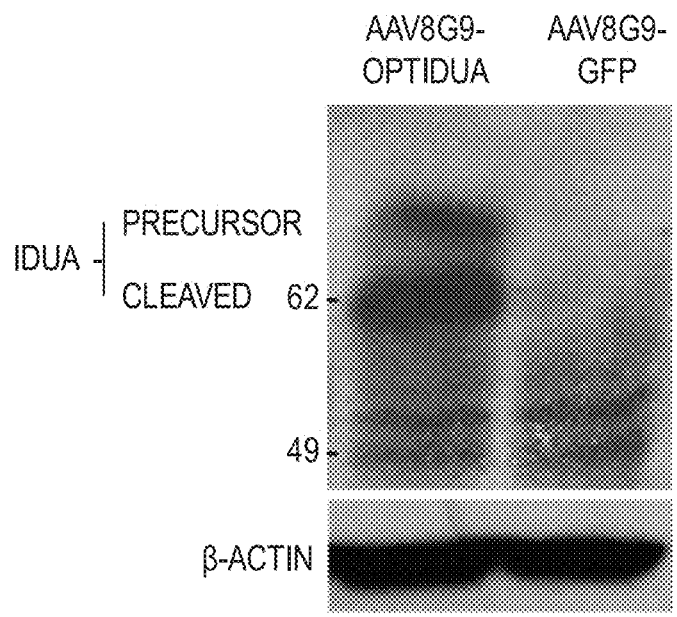
Figure 5C:
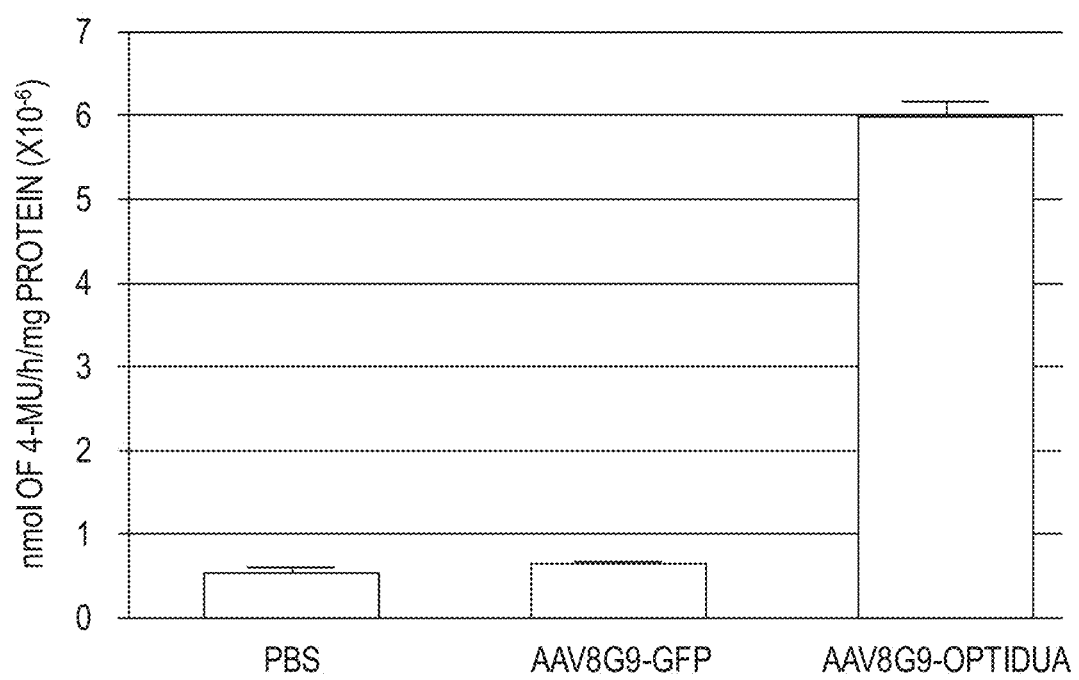

Next, AAV8G9-opt-IDUA preclinical vector preparations were produced by the UNC Vector Core and evaluated in normal human corneas ex vivo. For these experiments, injection of single-strand AAV8G9-GFP was evaluated and PBS served as the negative control. Seven days post-injection ($1e^{10}$ vg in 50 µl), total protein was recovered and IDUA abundance was investigated by Western blotting. In whole corneal lysates, it was observed that the resting levels of IDUA are relatively low and that vector-derived IDUA, both the precursor and cleaved forms, was readily detected (FIG. 5B). Consistently, a 10-fold elevation of IDUA activity was observed in the AAV8G9-opt-IDUA injected corneas when compared to normal levels found in human corneas (FIG. 5C).

By immunofluorescence staining and detection on human cornea cross sections, the resting levels and distribution of IDUA were determined (FIG. 6). As MPS I patient corneas are rare, staining under the same conditions but without the IDUA primary antibody served as the negative control. The results demonstrate relatively low levels of IDUA within the corneal stroma that were also present in the corneal epithelia and to a lesser extent, in the endothelial cell layer (FIG. 6). IDUA staining was also performed on human cornea cross sections that were injected with AAV8G9-opt-IDUA. The results correlate to those of the IDUA Western blot and the functional assay (FIGS. 5A-5C) in that there is an approximate 5-10 fold increase in IDUA in normal human corneas when administering AAV8G9-opt-IDUA compared to the resting level in human corneas (FIG. 6). Furthermore, similar to the results observed with AAV8G9-GFP, vector derived IDUA appeared well distributed (FIGS. 4B and 6).

Figure 7A:
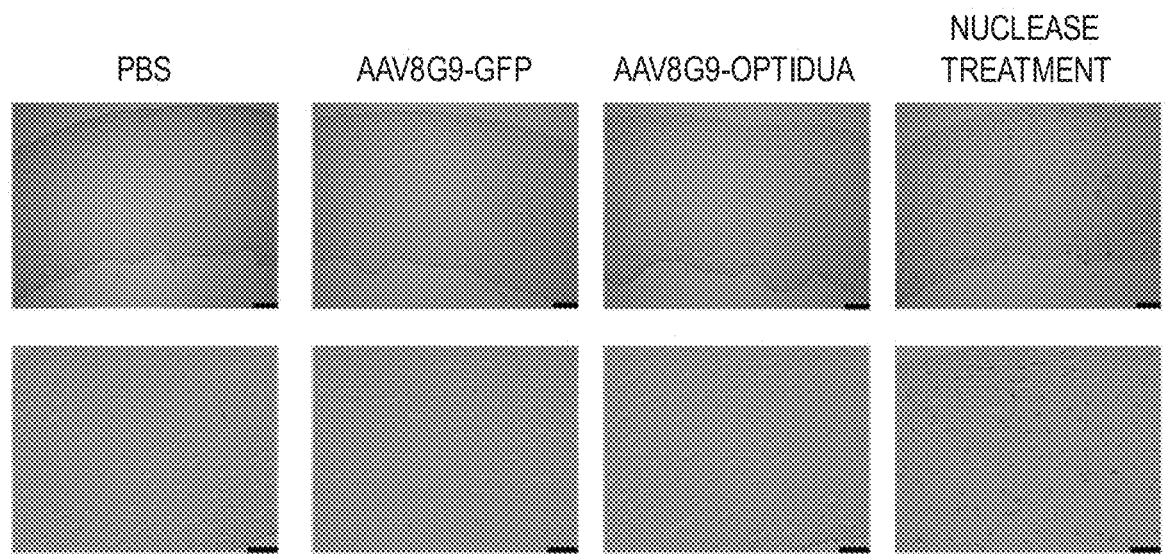
FIGS. 7A-7B show no cytotoxicity following AAV8G9-opt-IDUA injection in human corneas. (A) Human corneas injected with PBS, AAV8G9-GFP, or AAV8G9-opt-IDUA were processed 7 days later for Tunel staining. Top, images taken at 10×. Bottom, images taken at 20×. As a positive control, human corneas injected with PBS were nuclease treated. The scale bar is equal to 100 μm. (B) Quantitation of pixel area for total staining performed in (A). No statistical difference between cytotoxicity for corneas injected with AAV8G9-GFP or AAV8G9-opt-IDUA was observed ($p>0.05$).
Figure 7B:
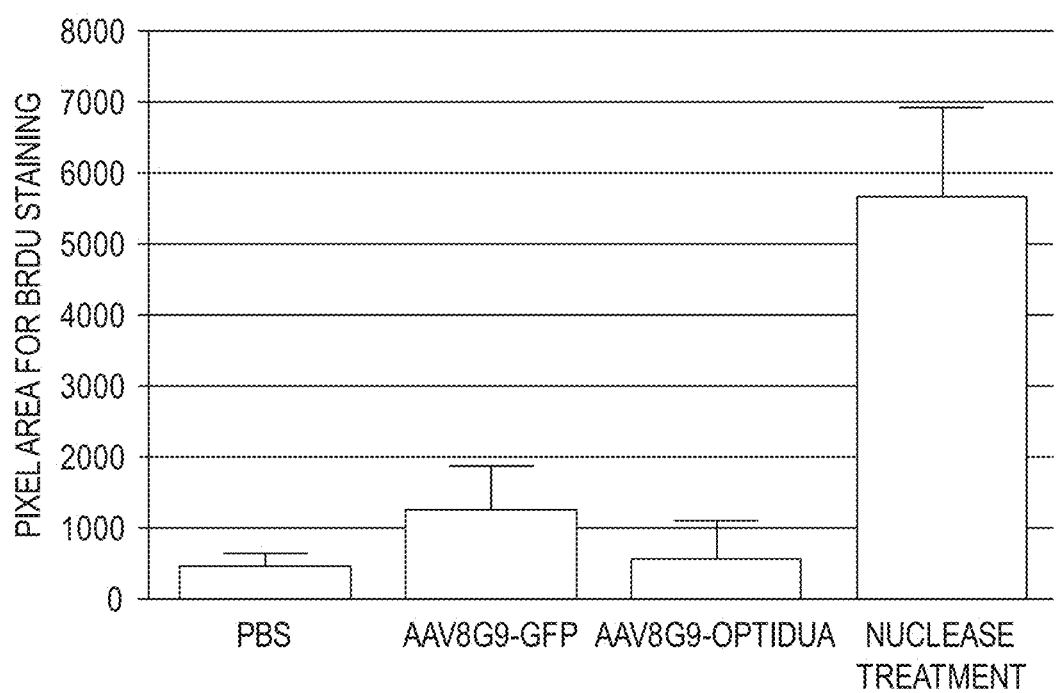

Cytotoxicity experiments were performed in normal human corneas and following ssAAV8G9-GFP or AAV8G9-opt-IDUA stromal injection (1e10 vg). Tunel staining, which detects fragmented DNA indicative of cellular apoptosis, was performed on day 7 post-injection. Although the nuclease-treated positive control sample demonstrated extensive Tunel staining, corneas in which IDUA abundance/function were significantly elevated were not significantly different than non-injected or AAV8G9-GFP injected corneas (FIG. 7). These results are consistent with those obtained using MPS I patient fibroblasts and collectively reinforce the safety of AAV8G9-opt-IDUA gene therapy in MPS I patient corneas.

Hematopoietic stem cell transplantation, after myeloablative chemotherapy using allogeneic bone marrow or umbilical cord blood donors has been shown to extend life and improve its overall quality, particularly when performed in MPS I children under 2 years of age (Shapiro et al., *J. Inherit. Metab. Dis.* 18(4):413 (1005);

Whitley et al., *Am. J. Med. Genet.* 46(2):209 (1993); Prasad et al., *Blood* 112(7):2979 (2008); Boelens et al., *Bone Marrow Transplant.* 43(8):655 (2009); Summers et al., *Ophthalmology* 96(7):977 (1989)). Engrafted donor cells provide a source of systemic IDUA and, through engraftment of donor microglial cells, enzyme replacement in the brain. Transplanted children, surviving 1-2 decades after HSCT with full donor chimerism, have normal blood IDUA levels with normal, to near normal, cognitive and cardiac functions. Later, and ongoing, manifestations of MPS I after transplantation do occur and generally are limited to the joints, bones, and the eye, all of which are organs with lower profusion and lower delivery of donor-derived IDUA. As such, our preclinical corneal approach explored herein, was designed as a supplemental MPS I therapy to address the shortcomings of stem cell transplantation and AAV gene therapy targeting the CNS.

As MPS I patient corneas are rarely available, we initially investigated disease correction in MPS I patient fibroblasts. The data demonstrate restoration of IDUA function using a low vector dose. This is, in part, due to the relatively low level of IDUA in normal fibroblasts which is presumably sufficient for normal cellular physiology (FIG. 1). Consistently, the abundance of IDUA found in normal human corneas was also modest. In fact, in whole cornea lysates, IDUA abundance by Western blotting was not readily detected, however, tissue histology identified resting levels of IDUA in corneal epithelia, endothelia and the majority in multiple cell types found in the stroma (FIGS. 5 and 6). This evaluation of IDUA abundance and AAV-mediated restoration highlights a very important aspect to the present corneal gene therapy approach: mainly that only a low amount of IDUA is necessary to restore WT IDUA function in the corneas of MPS I children. The chosen AAV dose in the cornea explants (1e10 vg) was found to be excessive and resulted in a 10-fold supraphysiological elevation of IDUA function. However, even at this high IDUA level no toxicity was detected (FIGS. 5, 6, 7). Given the ability of secreted IDUA to cross-correct neighboring cells, the low resting levels in normal human corneas, and the efficiency of AAV8G9-opt-IDUA for human cornea transduction, the data herein suggest that a low vector dose will result in normal levels of IDUA in MPS I patient corneas. Furthermore, reported complications associated with a neutralizing antibody response to the IDUA transgene product (IDUA) are not anticipated as there are no antibodies in the human cornea (Hinderer et al., Mol. Ther. 23(8):1298 (2015)).

Given the collective data herein, restoring IDUA function in MPS I corneas seems quite feasible. Furthermore, it appears that AAV8G9 elicits IDUA production in stromal cells that naturally produce IDUA, as well as in the endothelial layer (FIG. 6). As the present AAV-opt-IDUA strategy is capable of transducing both of these compartments (FIG. 6), the likelihood of reversing or preventing MPS I-associated corneal blindness, as a supplemental therapy to HSCT or AAV systemic gene delivery remains a viable possibility.

Example 4

AAV IDUA Expression Cassette in Corneas In Vivo

The effect of AAV IDUA expression in vivo was tested in MPS1 canines. The left eye of dog 1-712 was injected with the AAV8G9-CMV-optIDUA (1e9 vg/μl) solution as shown in FIGS. 8A-8D. The needle tip of an insulin syringe was inserted into the corneal stroma (A) and the solution was injected gradually (B) until the full volume (65 μl) was administered (C). Immediately following the injection, an area of fluid retention was visible as clouding or edema of the axial cornea, covering 30% of the corneal surface (D). Ophthalmic ultrasound biomicroscopy allowed determination of central cornea thickness at the indicated timepoints (FIG. 8E). The distension seen two minutes after injection was resolved within two days.

Figure 9A:
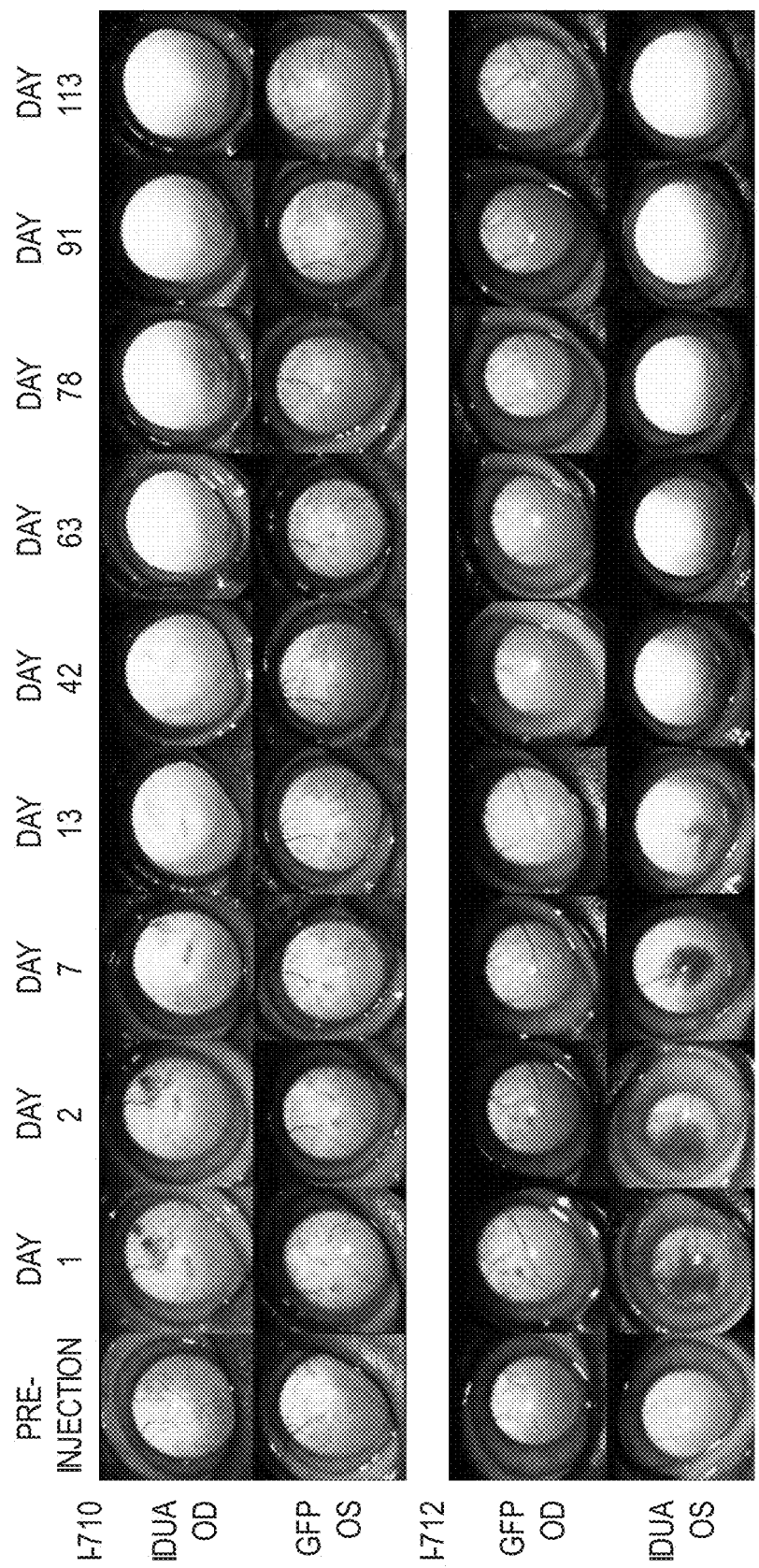
FIGS. 9A-9B show AAV8G9-CMV-optIDUA clears corneal cloudiness in MPS1 canines. A) MPS1 canines were administered AAV8G9-optIDUA in one eye while the contralateral eye was given AAV-GFP as a control, all by intrastromal injection. Improved reflectivity of the tapetum lucidum upon retroillumination of the fundus indicates cornea clarity over the indicated time period. B) Corneal edema and recovery. Dog 1-709 developed acute corneal edema first in the left eye at 5 weeks (image on the week of onset not shown), and then in the right eye at 10 weeks. Corneal edema subsided within 2-3 weeks while receiving topical steroid (TS) with or without systemic steroid (SS), and has not recurred in either eye for up to 19 wk post-injection. Importantly, the therapeutic effect remained evident in the IDUA-injected left eye after recovering from the transient immune reaction.

In the next experiment, two MPS1 canines were administered AAV8G9-optIDUA in one eye while the contralateral eye was given AAV-GFP as a control, all by intrastromal injection. Improved reflectivity of the tapetum lucidum upon retroillumination of the fundus indicates cornea clarity over the indicated time period (FIG. 9A). In both dogs, a substantial improvement in reflectivity was observed within 7 days and maintained for 113 days, demonstrating that IDUA expression cleared the corneal cloudiness.

Figure 9B:
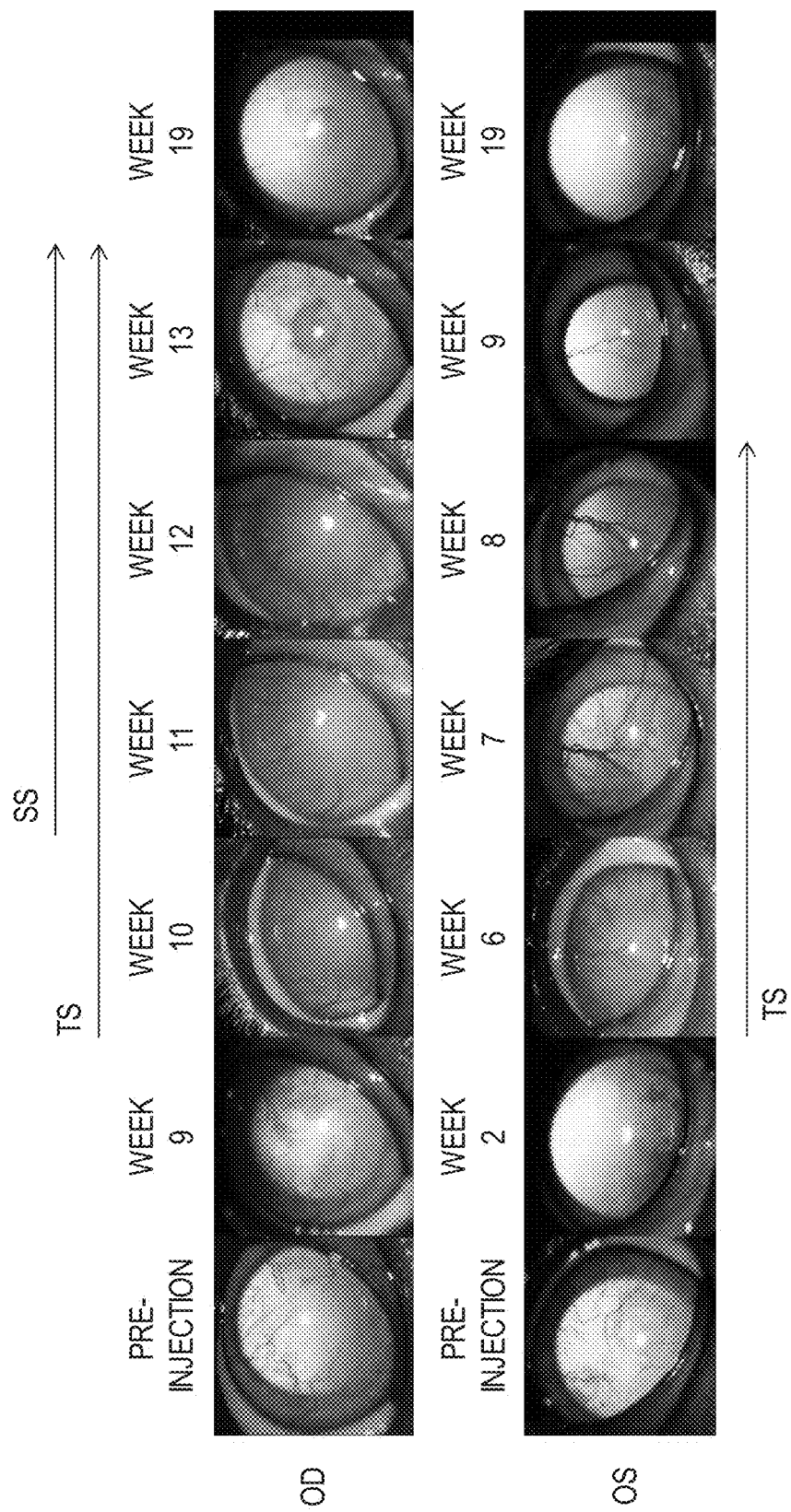

Dog 1-709 developed acute corneal edema first in the left eye at 5 weeks (image on the week of onset not shown), and then in the right eye at 10 weeks (FIG. 9B). Corneal edema subsided within 2-3 weeks while receiving topical steroid (TS) with or without systemic steroid (SS), and did not recurred in either eye for up to 19 wk post-injection. Importantly, the therapeutic effect remained evident in the IDUA-injected left eye after recovering from the transient immune reaction.

The foregoing is illustrative of the present invention, and is not to be construed as limiting thereof. The invention is defined by the following claims, with equivalents of the claims to be included therein.

That which is claimed is:

1. A recombinant nucleic acid comprising a sequence encoding human alpha-L-iduronidase (IDUA), wherein the nucleotide sequence has been codon-optimized for expression in human cells, and wherein the recombinant nucleic acid comprises a nucleotide sequence at least 90% identical to SEQ ID NO:1.

2. The recombinant nucleic acid of claim 1, comprising the nucleotide sequence of SEQ ID NO: 1.

3. An adeno-associated virus (AAV) vector genome comprising the nucleic acid of claim 1.

4. The AAV vector genome of claim 3, wherein the nucleic acid is operably linked to a constitutive promoter.

5. A cell in vitro comprising the AAV vector genome of claim 3.

6. The cell of claim 5, wherein the vector genome is stably incorporated into the cell genome.

7. An AAV particle comprising the AAV vector genome of claim 3.

8. The AAV particle of claim 7, wherein the AAV particle is an AAV2, AAV8, or AAV9 particle.

9. The AAV particle of claim 7, wherein the AAV particle is a chimeric AAV8/AAV9 particle.

10. A pharmaceutical formulation comprising the AAV particle of claim 7 and a pharmaceutically acceptable carrier.

11. A method of delivering IDUA to the cornea of a subject, comprising administering to the cornea of the subject an effective amount of the AAV particle of claim 7, thereby delivering IDUA to the cornea of the subject.

12. A method of treating mucopolysaccharidosis I (MPS I)-associated corneal clouding in a subject in need thereof, comprising administering to the cornea of the subject a therapeutically effective amount of the AAV particle of claim 7, thereby treating MPS I-associated corneal clouding in the subject.

13. A method of delivering IDUA to a cornea in vitro or ex vivo, comprising contacting the cornea with an effective amount of the AAV particle of claim 7, thereby delivering IDUA to the cornea.

14. The method of claim 13, further comprising transplanting the cornea to a subject in need thereof.

15. The method of claim 11, wherein the AAV particle is administered to the cornea by intrastromal injection.

16. The method of claim 11, wherein the AAV particle is administered to the cornea topically.

17. The method of claim 11, wherein the subject is a human subject.

* * * * *

UNITED STATES PATENT AND TRADEMARK OFFICE
CERTIFICATE OF CORRECTION

Page 1 of 1

PATENT NO. : 12,201,697 B2
APPLICATION NO. : 17/407718
DATED : January 21, 2025
INVENTOR(S) : Hirsch et al.

It is certified that error appears in the above-identified patent and that said Letters Patent is hereby corrected as shown below:

In the Specification

Column 4, Line 51: Please correct "1-709" to read --I-709--

Column 5, Line 22: Please correct "*Patent In*" to read --*PatentIn*--

Column 7, Line 31: Please correct "Pa." to read --PA.--

Column 29, Line 15: Please correct "across of" to read --across ≈50% of--

Column 31, Line 26: Please correct "1-712" to read --I-712--

Column 32, Line 18: Please correct "1-709" to read --I-709--

Signed and Sealed this
Eighth Day of July, 2025

Coke Morgan Stewart
*Acting Director of the United States Patent and Trademark Office*

SEQUENCE LISTING

```
<160> NUMBER OF SEQ ID NOS: 3

<210> SEQ ID NO 1
<211> LENGTH: 1993
<212> TYPE: DNA
<213> ORGANISM: Homo sapiens

<400> SEQUENCE: 1
caccggtcgc caccatgcga ccactgagac cacgggccgc tctgctggct ctgctggctt      60
cactgctggc cgctcccct gtcgctcctg ctgaggctcc ccacctggtg catgtggacg      120
cagctcgcgc cctgtggcca ctgaggagat tctggaggag cacaggcttt tgcccacctc      180
tgcctcacag ccaggctgac cagtacgtgc tgtcctggga tcagcagctg aacctggcat      240
atgtgggagc cgtcccccac aggggatca aacaggtgag aactcattgg ctgctggagc      300
tggtcaccac acgaggatct actggaaggg ggctgagtta caacttcacc cacctggacg      360
gctatctgga tctgctgaga gagaatcagc tgctgcctgg atttgaactg atgggctcag      420
ccagcggaca tttcaccgac tttgaggata agcagcaggt gttcgaatgg aaagacctgg      480
tcagctccct ggctcggcgc tacattgggc ggtatggcct ggcacacgtg agtaagtgga      540
actttgagac ttggaatgaa ccagaccacc atgacttcga taacgtgtca atgaccatgc      600 aggggttct gaattactat gatgcctgct ccgagggcct gcgggcagcc tctccagctc      660
tgcgactggg aggaccaggc gattccttcc acacaccacc cagaagtccc ctgtcatggg      720
gcctgctgcg gcactgtcat gacggaacca acttctttac aggagaagca ggggtgagac      780
tggattacat ctccctgcat cgaaagggg ccaggtctag tatctctatt ctggagcagg      840
aaaaggtggt cgctcagcag atccggcagc tgttccccaa atttgccgac acacctatct      900
acaatgacga ggctgatcct ctggtgggat ggtctctgcc tcagccatgg cgagccgatg      960
```

```
tgacttatgc tgcaatggtg gtcaaagtca ttgctcagca ccagaacctg ctgctggcaa    1020
atactaccag tgctttccca tacgcactgc tgagtaacga caatgccttc ctgtcatatc    1080 accccatcc ttttgcccag agaacactga ctgctcggtt tcaggtgaac aatacccgac    1140
ctccacatgt gcagctgctg aggaagcctg tcctgacagc catgggcctg ctggctctgc    1200
tggacgagga acagctgtgg gcagaggtgt ctcaggccgg gactgtcctg gatagtaacc    1260
acaccgtggg cgtcctggct tctgcacatc gacctcaggg accagcagac gcttggcgag    1320
cagctgtgct gatctacgca tcagacgata cacgagcaca ccctaaccga agcgtggcag    1380
tcactctgcg actgcgagga gtgccacctg gaccaggact ggtgtacgtc acccgctatc    1440
tggacaatgg cctgtgctct cccgatggag agtggcgaag gctggggagg cccgtgttcc    1500
ctacagcaga gcagtttaga cggatgagag cagccgaaga tccagtggct gcagcaccac    1560
gaccactgcc tgcaggaggc agactgaccc tgcggccagc cctgcgcctg ccaagcctgc    1620
tgctggtgca cgtctgcgca aggcctgaaa agccacccgg acaggtgaca aggctgagag    1680
ctctgccact gactcaggga cagctggtgc tggtctggtc agacgagcat gtggggagca    1740
aatgtctgtg gacttacgaa attcagttca gccaggatgg gaaggcctat acccctgtga    1800
gccggaaacc cagcaccttc aacctgttcg tcttttcccc agacaccggg gccgtgtccg    1860
gctcttaccg ggtccgcgct ctggactatt gggcaaggcc aggcccttc agcgatcctg    1920 tgccatacct ggaagtgcct gtgcctcgcg gcccaccatc tcctggaaac ccttgagggg    1980
atccgtcgac tag                                                       1993

<210> SEQ ID NO 2
<211> LENGTH: 20
<212> TYPE: DNA
<213> ORGANISM: Artificial
<220> FEATURE:
<223> OTHER INFORMATION: qPCR primer

<400> SEQUENCE: 2
caagtacgcc ccctattgac                                                  20

<210> SEQ ID NO 3
<211> LENGTH: 20
<212> TYPE: DNA
<213> ORGANISM: Artificial
<220> FEATURE:
<223> OTHER INFORMATION: qPCR primer

<400> SEQUENCE: 3
aagtcccgtt gattttggtg                                                  20
```